US 9,408,784 B2
Aug. 9, 2016

(12) United States Patent
Hilliard, Jr. et al.

(54) VISUALLY PATTERNED AND ORIENTED COMPOSITIONS

(71) Applicant: Colgate-Palmolive Company, New York, NY (US)

(72) Inventors: Peter R. Hilliard, Jr., Far Hills, NJ (US); Stacey Kaplan, New Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 132 days.

(21) Appl. No.: 14/156,532

(22) Filed: Jan. 16, 2014

(65) Prior Publication Data

US 2014/0199354 A1 Jul. 17, 2014

Related U.S. Application Data

(62) Division of application No. 13/518,963, filed as application No. PCT/US2010/061698 on Dec. 22, 2010.

(60) Provisional application No. 61/289,795, filed on Dec. 23, 2009.

(51) Int. Cl.
| | |
|---|---|
| *A61K 8/02* | (2006.01) |
| *A61K 8/03* | (2006.01) |
| *A61K 8/26* | (2006.01) |
| *A61Q 19/10* | (2006.01) |
| *A61Q 5/02* | (2006.01) |
| *A61Q 11/00* | (2006.01) |

(52) U.S. Cl.
CPC ............ *A61K 8/0241* (2013.01); *A61K 8/0237* (2013.01); *A61K 8/0245* (2013.01); *A61K 8/03* (2013.01); *A61K 8/26* (2013.01); *A61Q 5/02* (2013.01); *A61Q 11/00* (2013.01); *A61Q 19/10* (2013.01); *A61K 2800/26* (2013.01); *A61K 2800/262* (2013.01); *A61K 2800/87* (2013.01); *Y10T 428/268* (2015.01)

(58) Field of Classification Search
CPC ............ A61K 2800/26; A61K 8/0237; A61K 8/0241; A61K 8/0245; A61K 8/03; A61Q 11/00; A61Q 19/10; A61Q 5/02
See application file for complete search history.

(56) References Cited

U.S. PATENT DOCUMENTS

| | | | |
|---|---|---|---|
| 2,438,091 A | 3/1948 | Lynch | |
| 2,528,378 A | 10/1950 | Mannheimer | |
| 2,658,072 A | 11/1953 | Kosmin | |
| 3,859,227 A | 1/1975 | Dwyer | |
| 3,929,678 A | 12/1975 | Laughlin et al. | |
| 4,159,028 A | 6/1979 | Barker et al. | |
| 4,512,908 A | 4/1985 | Heile | |
| 5,059,414 A | 10/1991 | Dallal et al. | |
| 5,277,711 A | 1/1994 | Schmidt et al. | |
| 5,547,602 A | 8/1996 | Schuler | |
| 5,683,683 A | 11/1997 | Scafidi | |
| 5,776,435 A | 7/1998 | Gaffar et al. | |
| 5,862,996 A | 1/1999 | Crichton | |
| 5,906,205 A | 5/1999 | Hiebert | |
| 5,929,019 A | 7/1999 | Puvvada et al. | |
| 5,952,286 A | 9/1999 | Puvvada et al. | |
| 6,045,813 A | 4/2000 | Ferguson et al. | |
| 6,077,816 A | 6/2000 | Puvvada et al. | |
| 6,213,166 B1 | 4/2001 | Thibiant et al. | |
| 6,245,344 B1 | 6/2001 | Thibiant et al. | |
| 6,294,179 B1 | 9/2001 | Lee et al. | |
| 6,330,916 B1 | 12/2001 | Rickards et al. | |
| 6,367,519 B2 | 4/2002 | Thibiant et al. | |
| 6,426,326 B1 | 7/2002 | Mitra et al. | |
| 6,516,838 B2 | 2/2003 | Thibiant et al. | |
| 6,740,317 B1 * | 5/2004 | Cho et al. | ..................... 424/70.1 |
| 6,787,160 B2 | 9/2004 | Shacknai et al. | |
| 6,797,683 B2 | 9/2004 | Shana'a et al. | |
| 6,849,584 B2 | 2/2005 | Geary et al. | |
| 7,132,468 B2 | 11/2006 | Tepe | |
| 7,410,649 B2 | 8/2008 | Yoshimi et al. | |
| D608,647 S | 1/2010 | Toh et al. | |
| 2002/0119196 A1 | 8/2002 | Parikh et al. | |
| 2003/0003069 A1 | 1/2003 | Carson et al. | |
| 2003/0134759 A1 | 7/2003 | Geary et al. | |
| 2003/0152540 A1 | 8/2003 | Putman et al. | |
| 2003/0171230 A1 | 9/2003 | Shana'a et al. | |
| 2003/0190336 A1 | 10/2003 | Adams et al. | |
| 2003/0228270 A1 | 12/2003 | Tazberik et al. | |
| 2004/0047822 A1 | 3/2004 | Zamudo-Tena et al. | |

(Continued)

FOREIGN PATENT DOCUMENTS

| | | |
|---|---|---|
| EP | 1690878 B1 | 9/2007 |
| GB | 2046743 | 11/1980 |

(Continued)

OTHER PUBLICATIONS

*Technical Equipments in Modern Ceramic Industry* (editor in chief: Chen Fan, published by China Building Materials Press, 1999), p. 111. CN.
"Carribean Shower with Jojoba Beads Formula," 2007.
Ashby et al., 2000, "Pickering Emulsions Stabilised by Lapointe Clay Particles," Phys. Chem. Chem Phys. 2:5640-5646.
Dewhirst, 1980, "Structure-Activity Relationships for Inhibition of Prostaglandin Cyclooxygenase by Phenolic Compounds," Prostaglandins vol. 20(2):209-222.
Garcia et al., 2012, "Laponite-Stabilised Oil-in-Water Emulsions: Viscoelasticity and Thixotropy," Soft Matter 8:1609-1615.
Gong et al., 2006, "Aculyn™ 38 Rheology Modifier and Synergy with Lapoinite® Clay," Research Disclosure p. 704.
International Search Report and Written Opinion in International Application No. PCT/US08/057814, mailed Jul. 17, 2008.
International Search Report and Written Opinion in International Application No. PCT/US10/061698 mailed Feb. 21, 2012.

(Continued)

*Primary Examiner* — Sean Basquill
*Assistant Examiner* — Mark V Stevens

(57) ABSTRACT

Structured personal care compositions comprising a particle having an aspect ratio of greater than 1.5 are contemplated, as well as methods for using such compositions. The compositions provide a visually distinguishable, oriented pattern that is aesthetically pleasant to provide consumer appeal and product identification.

21 Claims, 4 Drawing Sheets

(56) References Cited

U.S. PATENT DOCUMENTS

| | | |
|---|---|---|
| 2004/0057920 A1 | 3/2004 | Focht et al. |
| 2004/0092415 A1 | 5/2004 | Focht et al. |
| 2004/0219119 A1 | 11/2004 | Wei et al. |
| 2004/0220063 A1 | 11/2004 | Chappell et al. |
| 2004/0223929 A1 | 11/2004 | Clapp et al. |
| 2004/0223991 A1* | 11/2004 | Wei et al. ............... 424/401 |
| 2004/0235693 A1 | 11/2004 | Wei et al. |
| 2004/0248748 A1 | 12/2004 | Wei et al. |
| 2005/0100570 A1 | 5/2005 | Wei et al. |
| 2005/0143268 A1 | 6/2005 | Midha et al. |
| 2005/0143269 A1 | 6/2005 | Wei et al. |
| 2005/0153852 A1 | 7/2005 | Evans et al. |
| 2005/0154083 A1 | 7/2005 | Hobbs et al. |
| 2005/0191337 A1 | 9/2005 | Gueret |
| 2005/0192187 A1 | 9/2005 | Wagner et al. |
| 2005/0233935 A1 | 10/2005 | Gunn et al. |
| 2005/0238680 A1 | 10/2005 | Stella et al. |
| 2005/0239670 A1 | 10/2005 | Stella et al. |
| 2005/0276768 A1 | 12/2005 | Wei et al. |
| 2005/0276829 A1 | 12/2005 | Stella et al. |
| 2006/0008438 A1 | 1/2006 | Velarde et al. |
| 2006/0027140 A1 | 2/2006 | Kniess et al. |
| 2006/0078524 A1 | 4/2006 | Midha et al. |
| 2006/0078527 A1 | 4/2006 | Midha et al. |
| 2006/0079417 A1 | 4/2006 | Wagner et al. |
| 2006/0079418 A1 | 4/2006 | Wagner et al. |
| 2006/0079419 A1 | 4/2006 | Wagner et al. |
| 2006/0079420 A1 | 4/2006 | Wagner et al. |
| 2006/0079421 A1 | 4/2006 | Wagner et al. |
| 2006/0079422 A1 | 4/2006 | Midha et al. |
| 2006/0088483 A1 | 4/2006 | Thevenet |
| 2006/0094628 A1 | 5/2006 | Wei et al. |
| 2006/0094635 A1 | 5/2006 | Pereira |
| 2006/0191589 A1 | 8/2006 | McCall et al. |
| 2006/0193921 A1 | 8/2006 | Brown et al. |
| 2006/0210505 A1 | 9/2006 | Clapp et al. |
| 2006/0234886 A1 | 10/2006 | Massaro et al. |
| 2006/0239945 A1 | 10/2006 | Bapat et al. |
| 2006/0239953 A1 | 10/2006 | Clapp et al. |
| 2006/0251606 A1 | 11/2006 | Coffindaffer et al. |
| 2006/0270584 A1 | 11/2006 | Frantz et al. |
| 2006/0276357 A1 | 12/2006 | Smith, III et al. |
| 2007/0009463 A1 | 1/2007 | Niebauer et al. |
| 2007/0009472 A1 | 1/2007 | Niebauer et al. |
| 2007/0010410 A1 | 1/2007 | Niebauer et al. |
| 2007/0014823 A1 | 1/2007 | Iwata |
| 2007/0044824 A1 | 3/2007 | Capeci et al. |
| 2007/0047383 A1 | 3/2007 | Williams et al. |
| 2007/0047384 A1 | 3/2007 | McLaughlin et al. |
| 2007/0071780 A1 | 3/2007 | Dubois et al. |
| 2007/0085063 A1 | 4/2007 | Capelli |
| 2007/0117729 A1 | 5/2007 | Taylor et al. |
| 2007/0141001 A1 | 6/2007 | Clapp et al. |
| 2007/0155637 A1 | 7/2007 | Smith, III et al. |
| 2007/0167338 A1* | 7/2007 | McHugh et al. ............ 510/130 |
| 2007/0183998 A1* | 8/2007 | Suzuki et al. ............. 424/63 |
| 2007/0248562 A1 | 10/2007 | Berry et al. |
| 2007/0249514 A1 | 10/2007 | Midha |
| 2007/0251603 A1* | 11/2007 | Olson ............ B29C 70/64 148/104 |
| 2007/0280976 A1 | 12/2007 | Taylor et al. |
| 2007/0286832 A1 | 12/2007 | Clapp et al. |
| 2007/0293411 A1 | 12/2007 | Focht et al. |
| 2008/0031084 A1 | 2/2008 | Williams et al. |
| 2008/0031085 A1 | 2/2008 | McLaughlin et al. |
| 2008/0031845 A1 | 2/2008 | Stella et al. |
| 2008/0033058 A1 | 2/2008 | Stella et al. |
| 2008/0039353 A1 | 2/2008 | Focht et al. |
| 2008/0045428 A1 | 2/2008 | Focht et al. |
| 2008/0045429 A1 | 2/2008 | Focht et al. |
| 2008/0051314 A1 | 2/2008 | Wenzel et al. |
| 2008/0242573 A1 | 10/2008 | Wei |
| 2008/0247968 A1 | 10/2008 | Sagel |
| 2009/0098367 A1 | 4/2009 | Wenzel et al. |
| 2010/0119562 A1* | 5/2010 | Hilliard et al. ............ 424/401 |

FOREIGN PATENT DOCUMENTS

| | | |
|---|---|---|
| GB | 2317932 | 4/1998 |
| JP | 6-183907 A | 7/1994 |
| JP | 6-194290 A | 7/1994 |
| JP | 2000-234950 A | 8/2000 |
| JP | 2003-201221 A | 7/2003 |
| WO | WO 97/23194 | 7/1997 |
| WO | WO 03/095600 | 11/2003 |
| WO | WO 2004/026276 | 4/2004 |
| WO | WO 2004/050055 | 6/2004 |
| WO | WO 2006/023591 | 3/2006 |
| WO | WO 2008/116147 | 9/2008 |
| WO | WO 2009/117013 | 9/2009 |

OTHER PUBLICATIONS

Jones, 2005, "Multifunction Synthetic Rheology Modifers for Personal Care Formulations: More Than Just Thickeners," Cosmetic Science Technology pp. 1-11.

Kwek et al., 2005, Aculyn T88 Rheology Modifier and Laponite® Clay, Research Disclosure pp. 1375-1376.

Laryea et al., "Stabilized Shampoo/Surfactant Suspensions," Research Disclosure, undated.

Rees, 2012, "New Route to Pickering Emulsions Stabilised Solely by Synthetic, Natural or Organically Modified Clay Particles," Research Disclosure Journal, Research Disclosure Database No. 577027, pp. 1-5.

Reeve, 2007, "Combinations of Acrylic Rheology Modifiers with Laponite® Clay for Suspension of Solids in Aqueous Surfactant Solutions," Research Disclosure Journal, Research.

Rockwood Additives, "Laponite in Personal Care Products," Laponite Technical Information, L211/01g, pp. 1-9, undated.

Rockwood Additives, "Laponite XLG: The Clear Leader," Product Bulletin/Laponite, undated.

Rockwood Additives, "Laponite: Performance Additives," pp. 1-22, undated.

Rockwood Additives, 2001, "Laponite® Performance-Focused Attributes in Rheology and Specialty Film Forming Applications," Rockwood Communiclay vol. 1(3):1-2.

Rohm and Haas Personal Care, "Aculyn™ Rheology Modifiers," Aculyn™ Product Comparisons, undated.

Rohm and Haas Personal Care, 2005, "Aculyn™88—More Than Just a Thickener!"

Rohm and Haas, 2006, "Aculyn™ 88 Rheology Modifier," http://www.rhpersonalcare.com/aculyn88_print_html.

Rohm and Haas, 2008, "Aculyn™ 88 Rheology Modifier," http://www.rohmhaas.com/personalcare/aculyn88_html.

Southern Clay Products, 2002, "Suspension Rhelogy for High Concentration Surfactant Cleansers," Poster Presentation.

Southern Clay Products, Inc., 2007, "Consumer Care Additives for Home Care & Personal Care Products," Rockwood Additives pp. 2-16.

"Suspension System for Personal Care Products Using Laponite XLG and XLS," 2000.

"Suspension System for Personal Care Products Using Laponite® XLS," 1997.

* cited by examiner

VISUALLY PATTERNED AND ORIENTED COMPOSITIONS

CROSS REFERENCE TO RELATED APPLICATIONS

This application is a divisional application of application Ser. No. 13/518,963, with a 371 entry date of 25 Jun. 2012, which is a national stage entry under 35 U.S.C. §371 of International Patent Application No. PCT/US2010/061698, filed 22 Dec. 2010, which claims priority to U.S. Provisional Patent Application No. 61/289,795, filed on 23 Dec. 2009, which are incorporated herein by reference.

BACKGROUND

The present invention relates to compositions, and in particular to multi-phase compositions comprising visually distinguishable patterns formed from particles dispersed, oriented, and suspended in at least one of the phases.

Personal care compositions that are suitable for cleansing the skin, e.g., soaps, shampoos, gels, moisturizers, and the like, are packaged in a variety of containers. Recently, the packaging for these products has been clear so that the consumer can see the product on the shelf prior to purchase. Some products are available in which visibly distinguishable phases can be seen, in which the phases are swirled together. Various dentifrice compositions, including toothpaste formulations, also are available in visibly distinguishable phases, sometimes seen through clear or translucent packaging.

Accordingly, there is an ongoing need for personal care compositions that deliver beneficial agents to the skin during use, are stable during storage, and present visibly distinguishable characteristics that can distinguish the products for consumers, and provide product recognition for the manufacturer. There also is an ongoing need for dentifrice compositions that deliver beneficial agents to the oral cavity, are stable during storage, and present visibly distinguishable characteristics that can distinguish the products for consumers, and provide product recognition for the manufacturer.

In addition, there is a desire for personal care compositions such as liquid soaps, shower gels, dentifrices, and body washes that can deliver skin benefit agents to the skin, that can deliver other beneficial agents to the area of application, and that have a visibly distinguishable characteristic.

BRIEF SUMMARY

In one embodiment, a particle oriented composition comprising visible particles having an aspect ratio greater than 1.5:1, wherein at least 50% of the visible particles have their x-y planes substantially parallel, parallel, or coincident to x-y planes of the other visible particles.

A visually patterned oriented composition comprising:
a) at least a first visually distinguishable zone comprising visible particles having an aspect ratio greater than 1.5:1, the visible particles having their larger dimension oriented in a plane substantially parallel to the plane of flow of the first visually distinguishable zone; and
b) at least a second visually distinguishable zone in physical contact with the at least first visually distinguishable zone, wherein the at least first visually distinguishable zone and the at least second visually distinguishable zone form a visibly distinguishable pattern,
wherein the at least first visually distinguishable zone and the at least second visually distinguishable zone form a visibly distinguishable pattern.

In another aspect, a method of making a visually patterned oriented composition comprising:
a) preparing at least a first composition comprised of a first vehicle and visible particles having an aspect ratio greater than 1.5:1;
b) preparing at least a second composition comprised of at least a second vehicle; and
c) dispensing the at least first composition and the at least second composition into a container in a manner that provides at least a first visually distinguishable zone comprised of the at least first composition in which the visible particles are oriented in a plane substantially parallel to the plane of flow of the first composition, and at least a second visually distinguishable zone comprised of the at least second composition, the at least second visually distinguishable zone in contact with the at least first visually distinguishable zone,
wherein the at least first visually distinguishable zone and the at least second visually distinguishable zone form a visibly distinguishable pattern.

BRIEF DESCRIPTION OF THE DRAWINGS

FIG. 1 is an image, and FIG. 1A is a schematic of the image.

DETAILED DESCRIPTION

Figure 1:
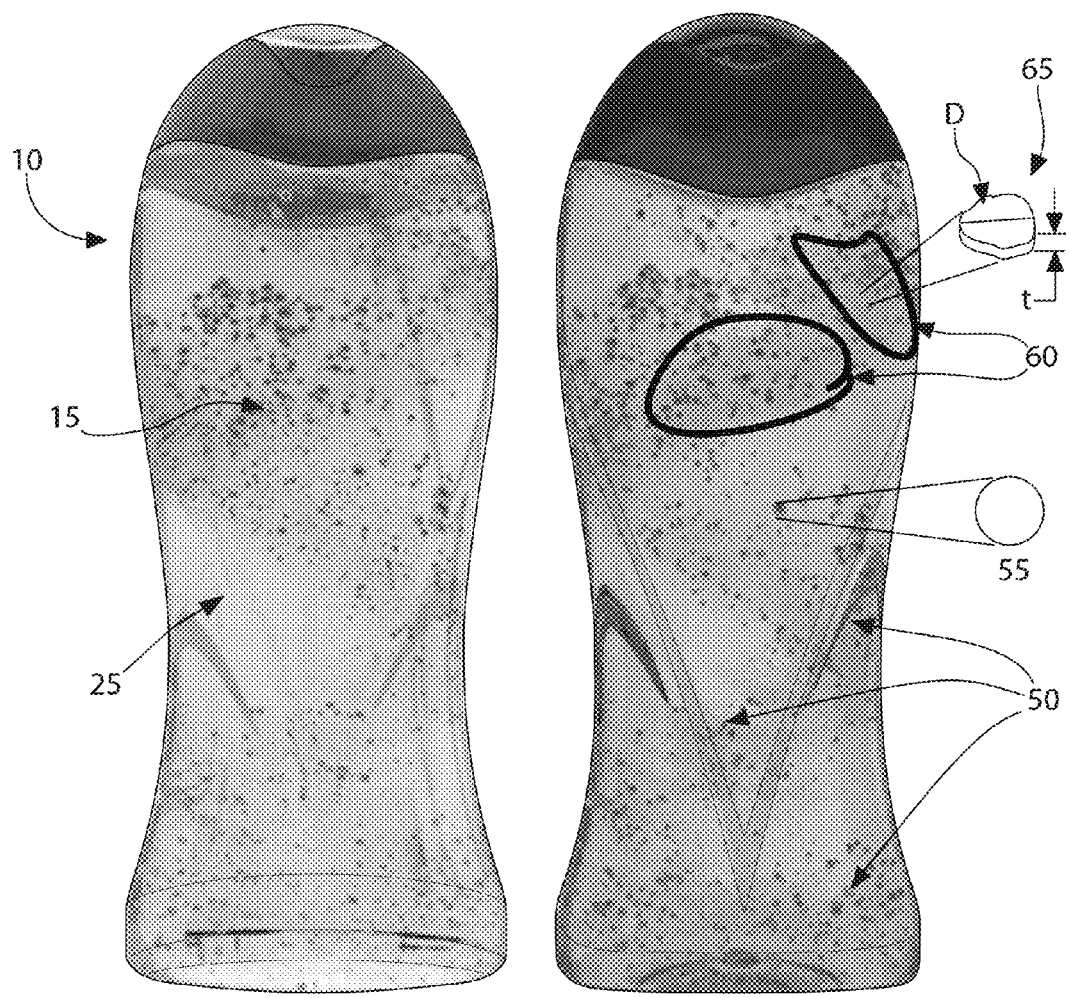
FIGS. 1 and 1A show two views (front and back) of a container including a visually patterned and oriented composition, in which at least one composition includes both oriented particles and visible beads.

As used throughout the present disclosure, ranges are a shorthand for describing each and every value that is within the range. Any value within the range can be selected as the terminus of the range. In addition, all references cited in the present disclosure are hereby incorporated by reference in their entireties. In the event of any conflict between a definition in the present disclosure and that of a cited reference, the present disclosure controls.

As used throughout this specification and claims, except as noted below in the examples, the amount of material listed is the active weight of the material. The expression "personal care composition" as used herein, refers to compositions intended for topical application to the skin and hair.

As described below, several embodiments will be for a multiphase composition. The present invention can also orient visible particles in a composition having a uniform composition.

The terms "multiphase" or "multi-phase" as used herein, are meant that the compositions occupy separate but distinguishable physical spaces inside the package in which they are stored, but are in direct contact with one another (i.e., they are not separated by a barrier and they are not emulsified or mixed to any significant degree). In one embodiment, the "multi-phase" personal care compositions comprise at least two visually distinguishable phases that are present within the container as a visibly distinguishable pattern formed as a result of visible particles being present in at least one of the visually distinguishable phases. The pattern results from the combination of the "multi-phase" composition by a method of manufacture herein described. The "visibly distinguishable patterns" include but are not limited to the following examples: striped, marbled, rectilinear, interrupted striped, check, mottled, veined, clustered, speckled, geometric, spotted, ribbons, helical, swirled, arrayed, variegated, textured, grooved, ridged, waved, sinusoidal, spiral, twisted, curved, cycle, streaks, striated, contoured, anisotropic, laced, weave or woven, basket weave, spotted, and tessellated. In certain embodiments, the pattern is selected from swirled, striped, geometric, marbled, and combinations thereof.

In certain embodiments, one composition in a multiphase composition can be clear or non-opaque and the another composition can be opaque. In certain embodiments, the visible particles can be included in the clear or non-opaque composition. The opaque composition can be made by including a sufficient amount of oil in the composition or other opacifying actives such as Titanium Dioxide, Lytron, etc.

The term "visually distinguishable phase" as used herein, refers to a region of a multiphase personal care composition having one average composition, as distinguishable from another region having a different average composition, wherein the regions are visible to the unaided naked eye. This would not preclude the distinguishable regions from comprising two similar compositions where one composition could comprise pigments, dyes, particles, and various optional ingredients, hence a region of a different average composition. For example, each composition could be the same except for a difference in pigment or dye, or each composition could be the same except for the particles. A phase generally occupies a space or spaces having dimensions larger than the colloidal or sub-colloidal components it comprises. A phase can also be constituted or re-constituted, collected, or separated into a bulk phase in order to observe its properties, e.g., by centrifugation, filtration or the like.

At least one visually distinguishable composition of the personal care compositions of the present invention comprises particles having an aspect ratio greater than 1.5:1, which means that the particles have a dimension in its cross-sectional area that is greater than the thickness of the particle.

Particles are defined by measurements in an x, y, and z coordinate system, with each axis being perpendicular to the other axes. The x axis is the longest (major) axis of the particle. The y axis is the next longest axis, and the z axis is the shortest axis (usually the thickness of the particle).

In certain embodiments, at least 50% of the particles have their x-y planes parallel or coincident to the x-y planes of the other particles. This means that the planes either do not intersect or they would be in the same plane. In another embodiment, the x-y planes are substantially parallel to each other in which the x-y planes are in the same plane or do not intersect when the planes are extended to the walls of the container that the composition is in. At some point, the planes could intersect, but they do not intersect in the limited space of the container. In other embodiments, at least 60, at least 70, at least 80, at least 90, at least 95, at least 99, or 100% of the particles have their x-y planes parallel, coincident, or substantially parallel to the x-y planes of the other particles.

"Aspect ratio," as it is used herein, denotes the ratio of the average major axis (x axis) of particles to the average thickness of the particles (z axis). As shown in FIG. 1, the expanded view of a particle is shown at 65, and the aspect ratio of particle 65 would be the ratio of D to t, or D/t. Accordingly, a particle with an aspect ratio greater than 1.5 will be flatter than a sphere, and, in certain embodiments, will have a tabular shape. In certain embodiments, the aspect ratio is about 2:1 or greater, about 3:1 or greater, at least 5:1, at least 10:1, at least 15:1, at least 17:1, or at least 24:1. Various particles having such an aspect ratio may be used in the invention, and include, for example, thin films, reflective metal particles, mica particles, deformable "visible beads," and the like.

At least a portion of the suspended material is of any size that is viewable by a person. By viewable it is meant that the suspended material can be seen by a non-color blind person with an unaided eye at 20/20 or corrected to 20/20 with glasses or contact lenses at a distance of 30 cm from the composition under incandescent light, florescent light, or sunlight. In other embodiments, at least 50%, at least 60%, at least 70%, at least 80%, at least 90%, at least 95%, or at least 99% of the particles are viewable by a person. In one embodiment, the particle size is 100 to 2500 microns in a longest dimension of the suspended material. In another embodiment, the particle size is 250 to 2250 microns. In another embodiment, the particle size is 500 to 1500 microns. In another embodiment, the particle size is 700 to 1000 microns. In another embodiment, a combination of more than one particle size can be used.) A "visible particle" is a particle that can be distinctively detected as an individual particle by the naked eye when comprised in the present composition, and which is stable in the present composition. The visible particle can be of any size, shape, or color, according to the desired characteristic of the product, so long as it is distinctively detected as an individual particle by the naked eye. Generally, a visible particle has a particle size of 50 µm to 5000 µm, and in certain embodiments 100 µm to 3000 µm or 300 µm to 1000 µm in a longest dimension. By stable, it is meant that the visible particles are not disintegrated or separated under normal shelf conditions. In one embodiment, the visible particle comprises visible beads, which typically have the shape of a small round ball. The visible beads may be present as conventional beads, or may be formulated to have a deformable shape in which the stresses placed on the beads during the filling process cause the beads to flatten and orient themselves in a direction parallel to the direction of flow. Both types of beads may be used alone or in combination with one another, in accordance with the various embodiments.

The visible particles may be incorporated in the at least one visibly distinguishable composition at levels of 0.01% to 25%, 0.01% to 5%, or 0.05% to 3%, by weight of the composition. The visible particle herein will typically comprise a structural material, and, in certain embodiments, an encompassed material.

As used herein, the term "yield point" (used interchangeably with "yield value") refers to a measurement of structure forming potential of a formula, i.e., the ability to suspend materials (such as oils, particles, beads, etc.) with densities that differ from those of the base material. For example, if a particle has a density greater than the density of the base material into which it is dispersed, the particle will have a tendency to sink to the bottom, thus creating a sinking force (the opposite is true for particles having a density less than the base material, in which case they have a tendency to rise or float, thus creating a buoyancy force). The yield point of the composition is the ability of the composition to counteract the force created by the particle, and consequently, fix the particle in its place in the composition so that it does not sink or rise, as the case may be. In various embodiments, the compositions of the present invention have yield points of at least 3 PA. In other embodiments, the yield point is at least 5 Pa at room temperature. As used throughout this specification and in the claims, yield point is measured using a Brookfield YR-1 Yield Rheometer with a number 73 vane. In various embodiments, the yield point of the compositions of the present invention are 3 to 100 Pa, 5 to 100 Pa, 10 to 100 Pa, 20 to 80 Pa, or 30 to 70 Pa. In certain embodiments, this can be measured at 24 hours or later after manufacturing.

As used throughout, "room temperature" refers to 23° C.±1.

As used throughout this specification and in the claims, the viscosity is measured in mPas (cps) at room temperature with a Brookfield DV-II viscometer using a number 6 spindle rotating at 10 rpm for 30 seconds.

The compositions described herein that contain the particles having an aspect ratio greater than 1.5:1, typically will include a structural material that serves to provide a certain strength to the composition so that the particles retain their distinctively detectable orientation in the present composition under ordinary transport, storage, shelf conditions, and use. By "ordinary" it is meant that which typically occurs during the aforementioned situations, and does not include vigorous shaking of the container that includes the compositions. Vigorous shaking of the container likely will cause the phases to coalesce into one another and the particles to become more evenly distributed through both phases, thus decreasing or even destroying the product's visibly distinguishable pattern. In one embodiment, the structural material further can be broken and disintegrated with very little shear on the hand with the fingers upon use.

The particles useful in the present invention that have an aspect ratio greater than one are those that are visible through the walls of an opaque, translucent or clear container or packaging. These particles usually are reflective particles that can be seen when viewed at the appropriate angle, but will change reflectance when viewed from a different angle. For example, tabular mica particles appear as bright flecks in a solution or slurry when light reflects off its major dimension, but may seem to disappear when viewed from the side, along its thickness, which is smaller than its cross-sectional area. Accordingly, when tabular reflective particles having an aspect ratio above 1 are oriented along the flow of the composition into which they are dispersed, they will appear differently depending on the angle upon which the viewer is viewing the product. A product container on a shelf therefore may catch a consumer's eye as the consumer views the product while walking along an aisle in a store, for example. Turning the product may reveal color changes, changes in reflectance, changes in the apparent intensity of reflected light, or may even appear to make the particles disappear from view.

Examples of particles that may be suitable for the present compositions include any discrete and visually distinguishable forms of matter that may be useful in a personal care composition or in a dentifrice. For example, useful particles include, without limitation: beads, encapsulates, particles made of polymer materials (e.g., plastic, in any desirable shape that appeals to consumers), metals (e.g., foil material or flakes, glitter), minerals (e.g., salts, rocks, pebbles, lava, glass/silica particles, talc), plant materials (e.g., pits or seeds of vegetables or fruits, plant fibers, stalks, stems, leaves or roots) and the like. In contrast to most particles dispersed in dentifrice and multi-phase personal care compositions, which typically are spherical in shape, the inventive particles have an aspect ratio (greater than 1.5, about 2:1 or greater, about 3 or greater, greater than 4, greater than 5, or greater than 10), that causes the particles to become oriented in substantially the same direction as the flow of the composition in which they are dispersed. In certain embodiments, the particles are mica, silicates, borosilicates, or glass.

Particles having an aspect ratio greater than 1.5:1 include one or more particles selected from films, metallic particles, naturally reflective particles, interference pigments, multi-layered pigments, solid and liquid crystals, deformable visible beads, and mixtures or combinations thereof. Suitable films may include polymeric films having reflective characteristics when viewed at an appropriate angle. Suitable metallic particles may include, for example, silver, gold, titanium, copper, or other reflective metallic particles. Suitable natural particles include, for example, mica, shale, coal, iron pyrite, silicates, borosilicates, glass, and the like.

Interference pigments useful in the present invention include pigments with pearl gloss prepared by coating the surface of a particle substrate material with a thin film. The particle substrate material is generally platelet in shape. The thin film is a transparent or semitransparent material having a high refractive index. The high refractive index material shows a pearl gloss resulting from mutual interfering action between reflection and incident light from the platelet substrate/coating layer interface and reflection of incident light from the surface of the coating layer. The interference pigments in certain embodiments comprises no more than 50 weight percent of the composition, no more than 30 weight percent, no more than 23 weight percent, or no more than 10 weight percent of the composition.

The interference pigments are platelet particulates. The platelet particulates of the multi-phased personal care compositions in certain embodiments have a thickness of no more than 2 µm, no more than 1 µm, or no more than 0.5 µm. The platelet particulates in certain embodiments have a thickness of at least 0.005 µm, at least 0.01 µm, or at least 0.05 µm.

The particle size determines the opacity and luster. The particle size is determined by measuring the diameter of the particulate material. The term "diameter" as used herein, means the largest distance across the major axis of the particulate material. Diameter can be determined by any suitable method known in the art, such as particle size analyzer Mastersizer 2000 manufactured by Malvern Instruments. The interference pigment in certain embodiments have an average diameter not greater than 200 µm, not greater than 150 µm, not greater than 100 µm, or not greater than 75 µm.

The interference pigment in certain embodiments are comprised of a multilayer structure. The center of the particulates typically is a flat substrate with a refractive index (RI) normally below 2. A wide variety of particle substrates are useful herein, including, for example, natural mica, synthetic mica, graphite, talc, kaolin, alumina flake, bismuth oxychloride, silica flake, glass flake, ceramics, titanium dioxide, $CaSO_4$, $CaCO_3$, $BaSO_4$, borosilicate and mixtures thereof, and in certain embodiments, mica, silica and alumina flakes.

A wide variety of thin films may be used to formulate the interference pigments. Nonlimiting examples are $TiO_2$, $Fe_2O_3$, $SnO_2$, $Cr_2O_3$, ZnO, ZnS, ZnO, SnO, $ZrO_2$, $CaF_2$, $Al_2O_3$, BiOCl, and mixtures thereof or in the form of separate layers, and in certain embodiments, $TiO_2$, $Fe_2O_3$, $Cr_2O_3SnO_2$. For the multiple layer structures, the thin films can be consisted of all high refractive index materials or alternation of thin films with high and low RI materials with the high RI film as the top layer.

The interference color is a function of the thickness of thin film, the thickness for a specific color may be different for different materials. For $TiO_2$, a layer of 40 nm to 60 nm or a whole number multiple thereof gives silver color, 60 nm to 80 nm yellow color, 80 nm to 100 nm red color, 100 nm to 130 nm blue color, 130 nm to 160 nm green color. In addition to the interference color, other transparent absorption pigments can be precipitated on top of or simultaneously with the $TiO_2$ layer. Common materials are red or black iron oxide, ferric ferrocyanide, chromium oxide or carmine. It was found that the color of the interference pigment in addition to its brightness had a significant influence on human perception of skin tone. In certain embodiments, colors are silver, gold, red, green and mixtures thereof.

The particles for use in the compositions of the invention also may include visible beads. The visible beads can be solid or liquid, filled or un-filled, as long as they are stable in the present composition. The material used for making the visible beads varies depending on the compatibility with other components, as well as material, if any, to be encompassed in the visible beads. The material also varies depending on whether the bead is to be designed as a deformable bead, or simply used as a generally spherical bead. Exemplary materials for making the visible beads herein include: polysaccharide and saccharide derivatives such as crystalline cellulose, cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, gum acacia (gum arabic), agar, agarose, maltodextrin, sodium alginate, calcium alginate, dextran, starch, galactose, glucosamine, cyclodextrin, chitin, amylose, amylopectin, glycogen, laminaran, lichenan, curdlan, inulin, levan, pectin, mannan, xylan, alginic acid, arabic acid, glucommannan, agarose, agaropectin, prophyran, carrageenen, fucoidan, glycosaminoglycan, hyaluronic acid, chondroitin, peptidoglycan, lipopolysaccharide, guar gum, starch, and starch derivatives; oligosaccharides such as sucrose, lactose, maltose, uronic acid, muramic acid, cellobiose, isomaltose, planteose, melezitose, gentianose, maltotriose, stachyose, glucoside and polyglucoside; monosaccharides such as glucose, fructose, and mannose; synthetic polymers such as acrylic polymers and copolymers including polyacrylamide, poly(alkyl cyanoacrylate), and poly(ethylene-vinyl acetate), and carboxyvinyl polymer, polyamide, poly(methyl vinyl ether-maleic anhydride), poly(adipyl-L-lysine), polycarbonate, polyterephthalamide, polyvinyl acetate phthalate, poly(terephthaloyl-L-lysine), polyarylsulfone, poly(methylmethacrylate), poly(.epsilon.-caprolactone), polyvinylpyrrolidone, polydimethylsiloxane, polyoxyethylene, polyester, polyglycolic acid, polylactic acid, polyglutamic acid, polylysine, polystyrene, poly(styrene-acrylonitrile), polyimide, and poly(vinyl alcohol); and other material such as fat, fatty acid, fatty alcohol, milk solids, molasses, gelatin, gluten, albumin, shellac, caseinate, bees wax, carnauba wax, spermaceti wax, hydrogenated tallow, glycerol monopalmitate, glycerol dipalmitate, hydrogenated castor oil, glycerol monostearate, glycerol distearate, glycerol tristearate, 12-hydroxystearyl alcohol, protein, and protein derivatives; and mixtures thereof. The components herein, however, are substantially used to make the visible beads, and are not dissolved or dispersed in the bulk of the present composition under normal shelf conditions.

Materials useful in making non-deformable beads comprise components selected from polysaccharides and their derivatives, saccharides and their derivatives, oligosaccharides, monosaccharides, and mixtures thereof, and in certain embodiments, components from the above mentioned group wherein components having various water solubility are selected. In one embodiment, the structural material comprises lactose, cellulose, and hydroxypropyl methylcellulose. Materials useful in making deformable beads include polystyrene-containing (e.g., polystyrene divinylbenzene) beads such as those disclosed in U.S. Pat. Nos. 5,906,205 and 6,330,916. Other useful materials for forming a deformable beads are organogel particles as described in detail in U.S. Pat. No. 6,797,683.

Beads that are organogel particles may comprise a structural material selected from Poloxamer™ compounds (I.e. polyoxypropylene-polyoxyethylene block copolymer such as Pluronic™ F-127 available from BASF), waxes (e.g., beeswax, paraffin, water-insoluble wax, carbon-based wax, silicone wax, microcrystalline wax, etc.), triglycerides, acid triglycerides, polymers, fluoroalkyl (meth)acrylate polymers and copolymers, acrylate polymers, ethylene/acrylate copolymers, polyethylene, polypropylene polymers and copolymers, fatty acids, fatty alcohols, fatty acid esters, fatty acid ethers, fatty acid amides, alkylene polyhydric alcohols, fatty acid amide of an alkanolamine, glyceryl monostearate, (aryl-substituted) sugars, dibenzyl sorbitol (or mannitoal, rabbitol, etc.), condensates and precondensates of lower monohydric alcohols, trihydroic alcohols, lower polyglycols, propylene/ethylene polycondensates, and the like. In certain embodiments, the structural material for visible beads that are organogel particles include beeswax, carnauba wax, low molecular weight ethylene homopolymers (e.g. Polywax™ 500, Polywax™ 1000, or Polywax™ 2000 polyethylene materials available from Baker Petrolite Corp.), or paraffin wax. As an alternative, the structural material may be omitted such that the organogel particles are more easily deformed and oriented by the stresses generated by the high yield point composition during lamellar flow through the delivery conduit to the container to be filled.

The visible beads herein, deformable or otherwise may encompass, contain, or be filled with an encompassed material. Such encompassed material can be water soluble or water insoluble. Suitable encompassed materials include skin benefit agents as described herein such as: oils, emollients, skin conditioners, vitamins, amino acids, proteins and protein derivatives, herbal extracts, pigments, dyes, antimicrobial agents, chelating agents, UV absorbers, optical brighteners, silicone compounds, perfumes, humectants, and mixtures thereof. In one embodiment, water soluble components are selected as the encompassed material. The encompassed material also may include oral care agents such as antibacterial agents, whitening agents, anti-calculus agents, surfactants, thickeners, abrasives, liquid mouthrinse, flavorants, pigments, and the like, all of which are well known in the art. The encompassed materials herein are substantially retained within the visible beads, and are substantially not dissolved in the bulk of the present composition under normal shelf conditions.

Particularly useful commercially available non-deformable visible beads herein are those with tradenames UNISPHERE™ and UNICERIN™ available from Induchem AG (Switzerland), and Confetti Dermal Essentials available from United-Guardian Inc. (NY, USA). Unisphere and Unicerin particles are made of microcrystalline cellulose, hydroxypropyl cellulose, lactose, vitamins, pigments, and proteins. Upon use, the Unisphere and Unicerin particles can be disintegrated with very little shear on the hand with the fingers with practically no resistance, and readily dissolve in the composition, or they can be disrupted during the brushing process.

Suitable visible beads for incorporation in the present compositions are described in detail in U.S. Pat. No. 6,797,683 (organogel particles); U.S. Pat. No. 6,045,813 (rupturable beads); U.S. 2004/0047822 A1 (visible capsules); and WO 97/23194 (capsulated or particulated oily substances).

The compositions may also contain gas bubbles, such as air bubbles.

The compositions of the present invention may be prepared by any known or otherwise effective technique, suitable for making and formulating the desired multi-phase product form. It is effective to combine toothpaste-tube filling technology with a spinning stage design. Additionally, the present invention can be prepared by the method and apparatus as disclosed in U.S. Pat. No. 6,213,166, U.S. Pat. No. 4,159,028, or US Publication No. 2004/0219119. The method and apparatus allows two or more compositions to be filled with a spiral configuration into a single container. The container is placed on a static mixer and spun as the composition is introduced into the container.

Alternatively, it is effective to combine at least two phases by first placing the separate compositions in separate storage tanks having a pump and a hose attached. The phases are then pumped into a single combining section. Next, the phases are moved from the combining sections into the filling section to form a filled product container that exhibits a visually distinguishable pattern of the phases. The pattern is selected from striped, marbled, geometric, and mixtures thereof.

The compositions of the various embodiments can be packaged in a transparent or translucent package such that the consumer can view the pattern through the package. Because of the viscosity of the subject compositions it may also be desirable to include instructions to the consumer to store the package upside down, on its cap to facilitate dispensing, and to avoid tipping the container up and down and consequently, vigorously mixing the components, thus harming the aesthetic appeal of the product.

The compositions of the present invention in certain embodiments include a material that increases the yield point of the composition, typically a thickener or structured material, to provide a stable composition in which the particles are stably positioned within the composition. It has been discovered that certain compositions comprising a clay, a crosslinked polycarboxylate thickener and a quaternized polymer are advantageous as personal care formulations. In addition, such compositions may be useful as personal care compositions that exhibit aesthetically desirable attributes, such as, e.g., visually distinguishable areas or zones in which the particles are dispersed. The compositions may include one or more visibly distinguishable areas, for example, one area or two areas including two different types of particles, or different colored particles.

In one embodiment, the present invention includes a combination of three structurants in an aqueous composition to provide the combination of a highly structured composition with a desirable rheology to provide packaging and aesthetic benefits together with an ability to support the particles having an aspect ratio greater than 1. The three structurants comprise the clay, particularly a layered silicate clay, a crosslinked polycarboxylate thickener; and a quaternary polymer. The highly structured composition also assists in orienting the particles having an aspect ratio greater than 1 during transport of the respective phases to the container (e.g., when filling), by virtue of the stresses created by the structured composition during transport. While not intending on being bound by any theory of operation, the inventors believe that the flow of the structured phases is not turbulent, or of minimal turbulence, and as a consequence, the high aspect ratio particles will orient themselves in the direction of flow of the aqueous composition due to the flow directional stresses placed on the particles.

In one embodiment, the personal care composition is a body wash, a shower gel or a liquid hand soap. In another embodiment, the composition is a dentifrice in the form of a mouthrinse, toothpaste, gel, or foam. In the case of dentifrice compositions, the structured composition can be created by use of conventional thickening agents. In another embodiment, the composition is a dish liquid (light duty liquid), hard surface cleaner, fabric softener, or laundry detergent.

In certain embodiments, the thickening agents are chosen from carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthum gum, gum arabic, and gum tragacanth can be used as part of the thickening agent to further improve the texture. Thickening agents can be used in an amount of from 0.1% to 15%, by weight of the composition. Other conventional ingredients may be included in the aqueous composition, including humectants, binding agents, gelling agents, antibacterial agents, anti-calculus agents, surfactants and foaming aids.

In one embodiment, the structured aqueous gel component comprises 0.1 to 1 weight % of the clay, or 0.1 to 0.5 weight % of the clay; 1 to 7.5 weight % of the crosslinked polycarboxylate thickener; and 0.1 to 2 weight % of the quaternary polymer, each weight % being based on the weight of the composition.

The clay may comprise a sodium magnesium silicate, in particular a synthetic hectorite, such as a clay available under the trade name Laponite™ available from Southern Clay Products (Gonzales, Tex., USA). In one embodiment, the Laponite™ clay is Laponite™ XLG, which is a sodium magnesium silicate.

In another embodiment, the structurant may include a rheology modifier in the form of a cross-linked polymer, such as CARBOPOL® Aqua SF-1 polymer, commercially available from Lubrizol Corp., Wickliffe, Ohio. In yet another embodiment, the structurant may provide a close packed network of spherulites, such as the MIRACARE® SLB surfactant system, commercially available from Rhodia, Cranbury, N.J.

In one embodiment, the crosslinked polycarboxylate thickener comprises an acrylic crosslinked polycarboxylate thickener.

In one embodiment, the quaternary polymer has a molecular weight of less than 2,000,000 and a charge density of less than 6 meq/g at a pH of 7.

In one embodiment, each of the first and second structured aqueous gel components comprises 0.1 to 1 weight % of a clay, or 0.1 to 0.5 weight % of a clay; 1 to 7.5 weight % of a crosslinked polycarboxylate thickener; and 0.1 to 2 weight % of quaternary polymer, or 1 to 2 weight % of quaternary polymer, each weight % being based on the weight of the composition.

In one embodiment, each of the phases has the same composition of structurant, crosslinked polycarboxylate thickener and quaternary polymer, and the same amount of the emollient component, and the phases are visually distinguishable by comprising different particles therein, or one composition may comprise the particles and the other composition comprises no particles, or different particles, or non-deformable beads.

When a clay is used as the structurant, the phases formed using the clay form a structured gel composition, but at very low amounts of clay, typically from 0.1 to 1 weight %, more typically 0.1 to 0.5 weight %, yet more typically 0.3 weight %, clay based on the weight of the composition. This means that the composition may be clear or opaque, depending on the other components (e.g., particles having an aspect ratio greater than 1) in the composition apart from the system forming the structured gel, and can have good aesthetic properties, visual and tactile, for a personal care composition. Also, the low amount of clay reduces the cost of the composition. Yet further, the use of the low clay content structured gel composition significantly reduces the cost of providing a personal care composition that can support a high emollient oil content, to deliver a high degree of moisturization when applied to the skin, as compared to many current commercial personal care body wash, shower gel or liquid soap compositions. The aqueous composition can have a high water content, typically more than 50 weight % of the composition.

In the embodiment in which clay is used, the clay, particularly the layered silicate clay, can form a colloidal dispersion in water which can provide rheology modification for the aqueous composition so as to provide a thickened product with high shear thinning and a thixotropic rheology. The same is true when spherulites, or cross-linked polymer thickeners (Carbopol™) are used. The addition of a crosslinked polycarboxylate thickener, in particular an anionic thickener thereto can modify the rheology to stabilize and thicken the composition. The further addition of a quaternary polymer, greatly increases the yield point of the composition so that the formulation has a very high shear and is mechanically stable after manufacture and during transport to the consumer, and during use. However, the thixotropic properties of the composition ensure that the composition can readily be manufactured, for example by injection of the liquid composition from a nozzle into a container for delivery to the consumer, and can readily be used by the consumer when dispensing a desired amount or dose of the composition from the container. The quaternary polymer is typically present in an amount of 0.01 to 5 weight %, or 0.05 to 2 weight %, more typically 0.1 to 0.2 weight %, 0.108 weight % based on the weight of the composition, to achieve the desired increase in yield point of the structured gel formed from the clay, crosslinked polycarboxylate thickener and quaternary polymer.

Furthermore, benefit agents, in particular emollients to deliver a high level of moisturization for personal care products, are supported by the structured gel composition in a uniformly and highly dispersed manner, and there is no oil-in water emulsion. For oral care compositions, oral care actives and additives also are supported by the structured gel composition in a uniformly and highly dispersed manner, and there is no oil-in water emulsion.

Consequently, personal care compositions can support a high proportion of emollients, typically 3 to 30 weight %, more typically 5 weight %, emollient based on the weight of the composition, which can correspondingly deliver a high degree of moisturization to the skin when the composition is used, for example, as a body wash, shower gel or liquid hand soap, without the composition feeling oily or greasy to the touch.

Furthermore, even with a high amount of emollient the composition visually appears to have a consistent and uniform single phase composition, even if different visually distinguishable areas, distinguished by different coloration, for example, are provided. This is achievable in highly aqueous compositions, for example where water as a solvent for the gel composition comprises at least 50 weight % of the composition. High water content reduces the manufacturing cost of the composition.

The visually distinguishable areas may for example be achieved by simultaneously co-injecting the two visually distinguishable structured gel components into a common container or package from respective nozzles or from a single nozzle.

In addition, the provision of the highly structured gel composition provides a base formulation that can be employed in a number of different compositions, thereby reducing product development periods, and formulation and manufacturing costs, across a range of different products. For example, the composition can comprise liquid hand soaps, shower gels or body washes, dentifrices such as toothpastes, gels, foams, and mouth rinses, using the same base formulation, the products primarily varying in color and/or fragrance, and possibly also emollient content because the range of emollient content that can be supported within the composition is rather large, for example up to 15 weight % based on the weight of the composition.

The highly structured gel permits plural visually distinguishable areas to be present in the same container or package, and the areas can remain visually distinguishable during ordinary transport of the product from the manufacturer to the consumer because of the high yield point of the gel. There is no need to formulate the structured gels differently to provide two visually distinguishable areas, apart from providing different visual differences, such as differential coloration and/or the use of visible beads. This simplifies manufacture and reduces the manufacturing cost. However, the thixotropic nature of the gel readily permits both filling of the container or package during manufacture of the product and subsequent consumer acceptable dispensing of the composition from the container or package during use by the consumer.

In addition, it has been found that the structured gel can support a high amount of emollient which can deliver a high degree of moisturization to the skin yet without causing emollient, in the form of oil, to be deposited in significant amounts onto sanitary ware, such as bathtubs, shower cubicles and wash basins, which is clearly undesirable.

Some known personal care compositions, such as body washes and shower gels, that contain emollients for skin moisturizing can deliver a high degree of moisturization to the skin but correspondingly they also cause significant amounts of emollient to be deposited onto sanitary ware, which then requires frequent cleaning.

One particular advantage of the personal care compositions of the present invention is that two or more visually distinguishable areas can be provided which creates an attractive aesthetic appearance to the consumer. Moreover, the aesthetic appearance of two or more visually distinguishable areas can impart to the consumer the technical concept of the composition providing plural technical effects, for example moisturization and a cleaning action, each associated with a respective visually distinguishable area. Such a technical concept can be imparted even though the visually distinguishable areas have essentially the same composition, apart from those components that provide the visual distinction, such as different colorants or colorant contents. By virtue of the orientation of the particles having an aspect ratio greater than 1, the compositions also provide a unique aesthetic effect in which the color may appear differently depending on the angle from which the product is viewed. It also is possible that the product may appear clear when viewed from one angle, and colored from another angle. These unique aesthetic aspects of the inventive products may help attract a potential customer's eye when walking past the product on a shelf, in which the product may seem to change color, or provide a reflective glint in the viewer's eye.

The two or more visually distinguishable zones can provide the advantage that when, for example, an emollient system is incorporated into the composition, the emollient can be equally present in each visually distinguishable area, and so can be uniformly distributed throughout the composition, even though the consumer may visually perceive there to be only one of the visually distinguishable areas that would be expected to be formulated to provide the moisturizing effect. This means that a high level of emollient can be incorporated into the composition having two or more visually distinguishable areas without having to provide a relatively high emollient concentration composition and a relatively low, or even zero, emollient concentration composition, as in some known multiple phase compositions, and deliver better perceived benefits, aesthetics, and rheology.

Such known compositions may exhibit excessive emollient deposition onto sanitary ware, as discussed above, because of the need for an excessively high emollient content in one composition. Such known compositions may comprise an aqueous composition that comprises surfactants and delivers a cleaning benefit and an anhydrous composition or emulsion composition (a water-in-oil or oil-in-water emulsion) that comprises emollients and delivers a moisturizing benefit. In addition to the improved aesthetics achieved in accordance with the present invention, the compositions present an improvement over known compositions because the invention enable the use of higher concentrations, and more uniformly dispersed benefit agents.

In the present invention, there can be a single structured gel composition, having two visually distinguishable areas, commonly delivering both a cleaning benefit and a moisturizing benefit because both surfactants and emollients are dispersed throughout both visually distinguishable areas.

As used herein, the term "structured" refers to a composition in which the base, active material and structuring agent form a system with solid suspending properties while remaining pourable. Examples of structured systems include those wherein the active materials (such as detergents, surfactants, emollients, moisturizers, antibacterial agents, anticalculus agents, and the like) are dispersions of lamellar droplets in an aqueous composition that contains an electrolyte. These lamellar droplets are often referred to as an "onion-like" configuration or layering of surfactant molecules, for example, as spherulites. See, e.g., U.S. Patent Publication Nos. 2004/0092415, 2004/0223991, 2004/0235693 and 2004/0248748 which are directed to spherulite-based structured systems.

The structured compositions of the present invention may contain a clay, or cross-linked polymer and are hence directed to clay-based (rather than spherulite-based) structurant systems. Examples of useful classes of clays include, but are not limited to: kaolinites, smectites, illites and chlorites. In certain embodiments of the present invention, the clay may be useful as a thickener and/or structure building composition. For example, swelling clays such as smectites are particularly useful as structurants, and include, e.g., bentonite, hectorite, layered magnesium silicate (such as a clay available from Southern Clay Products (Gonzales, Tex., USA) under the trade name Laponite™); and magnesium aluminum silicate (such as a clay available under the trade name Veegum from various suppliers, USA). U.S. Pat. No. 6,787,160 to Schacknai et al. provides further discussion of natural and synthetic clays. A synthetic layered silicate, such as Laponite™ XLG, which is anionic. In various embodiments of the present invention, the amounts of clay present are 0.01 to 5%, 0.05 to 3%, 0.1 to 2% or 0.2 to 1% by weight of the total composition.

The compositions of the present invention also may comprise a mixture of surfactants, comprising at least one anionic surfactant and at least one amphoteric surfactant. Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678.

Useful anionic surfactants for the present embodiments include alkyl and alkyl ether sulfates, such as those that may have the respective formula $ROSO_3M$ and $RO(C_2H_4O)_xSO_3M$, wherein R is alkyl or alkenyl of from 8 to 24 carbon atoms, x is 1 to 10, and M is a water-soluble cation such as ammonium, sodium, potassium and triethanolamine. The alkyl ether sulfates may be made as condensation products of ethylene oxide and monohydric alcohols having from 8 to 24 carbon atoms. In one embodiment, R has from 10 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil can be used. Such alcohols are reacted with 1 to 10, or 3 to 5, or with 1.8, 2, or 3 molar proportions of ethylene oxide and the resulting mixture of molecular species having, for example, an average of 3 moles of ethylene oxide per mole of alcohol, is sulfated and neutralized.

Specific examples of alkyl ether sulfates include sodium and ammonium salts of coconut alkyl triethylene glycol ether sulfate; tallow alkyl triethylene glycol ether sulfate, and tallow alkyl hexaoxyethylene sulfate. In certain embodiments, alkyl ether sulfates are those comprising a mixture of individual compounds, said mixture having an average alkyl chain length of from 10 to 16 carbon atoms and an average degree of ethoxylation of 1 to 4 moles of ethylene oxide.

Other suitable anionic surfactants include water-soluble salts of the organic, sulfuric acid reaction products of the general formula $[R_1—SO_3-M]$, wherein $R_1$ is chosen from a straight or branched chain, saturated aliphatic hydrocarbon radical having from 8 to 24, or 10 to 18, carbon atoms; and M is a cation. Suitable examples include the salts of an organic sulfuric acid reaction product of a hydrocarbon of the methane series, including iso-, neo-, ineso-, and n-paraffins, having 8 to 24 carbon atoms, or 10 to 18 carbon atoms and a sulfonating agent, e.g., $SO_3$, $H_2SO_4$, oleum, obtained according to known sulfonation methods, including bleaching and hydrolysis, for example, alkali metal and ammonium sulfonated $C_{10-18}$ n-paraffins.

Useful anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, sodium tridecyl benzene sulfonate, sodium dodecyl benzene sulfonate, sodium and potassium salts of sodium pareth sulfate, sodium and potassium salts of sodium pareth ether sulfate, sodium trideceth sulfate and combinations thereof.

In one embodiment, the anionic surfactant comprises an ethoxylated sodium pareth sulfate, in particular SLES ($SO_3Na$ Pareth 145-2EO Sulfate Base-25.5% AI). In another embodiment, the anionic surfactant is an ethoxylated sodium laureth sulfate, in particular SLES($SO_3Na$ Laureth $C_{12-14}$ Alcohol-2EO Sulfate Base-70% or 25.5% AI)

Useful amphoteric surfactants include those that may be described as derivatives of aliphatic secondary and tertiary amines in which the aliphatic radical can be straight or branched chain and wherein one of the aliphatic substituents contains 8 to 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. Examples of useful amphoteric surfactants include amidobetaines, amidosulfobetaines, coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine.

In certain embodiments, the compounds of the present invention optionally further comprise a crosslinked polycarboxylate thickener. In one embodiment, the crosslinked polycarboxylate thickener is an acrylic crosslinked polycarboxylate rheology modifier, or an acrylates copolymer or derivative thereof or an acrylates/methacrylate cross polymer, for example an acrylates steareth-20 methacrylate crosspolymer. Useful crosslinked polycarboxylate thickeners include, for example, partially crosslinked polycarboxylate thickeners that may be partially substituted with at least one alkyl group, e.g., thickeners, which are anionic or nonionic, commercially available under the trade name Aculyn™ from Dow (for example, Aculyn™ 22, Aculyn™ 28, Aculyn™ 33, Aculyn™ 38, Aculyn™ 44, Aculyn™ 46, Aculyn™ 60, Aculyn™ 88 and the like). An anionic crosslinked polycarboxylate thickener, such as Aculyn™ 88, can be selected.

In certain embodiments, the compounds of the present invention optionally further comprise a polyhydric alcohol having an average molecular weight of less than 600. In various embodiments, the average molecular weight may be less than 550 or less than 500. Any polyhydric alcohol can be used, but examples of suitable polyhydric alcohols include glycerin (glycerol), ethylene glycol, diethylene glycol, propylene glycol, polypropylene glycol, polyethylene glycol, di- and tri-glycerin and/or poly-glycerin and combinations thereof. It has been found that where the polyhydric alcohol has a molecular weight of less than 600, the compositions are particularly advantageous in terms of desirability and ease of use for consumers. In addition, the addition of the polyhydric alcohol aids in the dispersion of the compositions during formulation, thereby leading to more efficient processing and higher yield of formula.

The compositions of the present invention may further comprise an optional preservative, such as, for example, EDTA. It has been discovered, that where the amounts of EDTA are varied, e.g., from 0 to 1 weight %, various characteristics can be optimized.

The compositions of the present invention also may comprise a quaternized polymer, i.e., a highly charged cationic polymer that may effectively build up the structure of the formula, increase yield point and further enhance the ability of the composition to support oils, emollients, particles and other inclusions in the compositions in a stable formulation. Examples of quaternized polymer that may be useful for the present embodiments include, e.g., the homopolymer of dimethyl diallyl ammonium chloride solid under the trade name MERQUAT™ 100 having a molecular weight lower than 100,000 and the copolymer of dimethyl diallyl ammonium chloride and acrylamide, having a molecular weight greater than 500,000 and sold under the name Merquat™ 500, as well as related compositions available under the following trade names: Merquat™ 5, Merquat™ 280, Merquat™ 550 (Polyquat 7), Merquat™ 2001, Merquat™ 3330 all available from Nalco Company (Napierville, Ill., USA); Conditioneze NT-2 (available from ISP Corp.), Jaguar (available from Rhodia Corporation).

In one embodiment, the quaternary polymer has a charge density at pH 7 of 1 to 5 meq/gm, or from 2 to 4 meq/gm, or 3 meq/gm, and a molecular weight of from 1,000,000 to 2,000,000, or 1,600,000. Such a quaternary polymer is provided by Merquat™ 550 (Polyquat 7).

The compositions of the present invention also may comprise at least one emollient oil that enhances the moisturization of the skin. Examples of such oils include vegetable triglycerides, maleated castor oils (such as that available under the trade name Ceraphyl™, e.g., Ceraphyl™ RMT, from ISP Corp.), maleated soybean oils, sunflower oils, soybean oils, mineral oils, petrolatum, silicones or silicone elastomers, or mixtures or derivatives thereof.

It has particularly been found by the present inventors that when the personal care compositions of the present invention comprise at least two emollient oils, comprising a mixture of a maleated oil, in particular a maleated castor oil (such as that available under the trade name Ceraphyl™, e.g., Ceraphyl™ RMT, from ISP Corp.), and another emollient selected from at least one of petrolatum, a vegetable oil such as sunflower oil, or a mixture thereof, then the efficacy of emollient moisturization of the skin, particularly after the skin has been dried of aqueous moisture, is increased as compared to when the same other emollient is used without the maleated oil. See example below.

It has further been found by the present inventors that the structured gel comprising the clay, the crosslinked polycarboxylate thickener, and the quaternary polymer sometimes has a high viscosity, particularly after a fragrance has been added thereto, which can present problems for manufacturing, consumer use and consumer acceptance. This can be a problem for personal care compositions such as body washes, shower gels and liquid hand soap cleansing products. It has further been found by the present inventors that the addition of fatty esters to the composition can reduce the viscosity of the composition.

In particular, the fatty esters may be selected from at least one of isopropyl myristate, isopropyl palmitate, and isopropyl isostearate.

During manufacture of the composition, it has been found that the order of addition of the components can significantly modify the effectiveness of the fatty ester as a viscosity modifier for the composition. For example, if the fatty ester is added immediately after the addition of the clay to the composition, then this can result in a larger reduction in viscosity of the composition than if the fatty ester is added immediately at the end of the formulation process and after the addition of the fragrance to the composition, In certain embodiments, the compositions of the present invention may be presented in visually distinguishable areas, e.g. as clouds, stripes or areas of varying opacity, such as, for example, wherein certain areas contain inclusions. In certain embodiments, the compositions are uniform in composition; however, they may exhibit a visually distinguishable appearance based on different amounts and/or types of colorants used or inclusions, for example. This distance may include, for example, arm's length, a distance from a consumer's eye to a store shelf, or 10 cm to 3 m or more. "Visually distinguishable" may include, for example, areas that are different colors, different shades of a color (i.e., different gradations of a color over the dimensions of the container or package), different opacities, contain different inclusions or particles, or different phases such as solid, liquid or gaseous (e.g., air bubbles). Also contemplated within the embodiments of the present invention are compositions wherein one or more of such areas is visually clear and/or contains no colorant. Visually distinguishable includes areas that are recognizably different because one may contain a particle having an aspect ratio greater than 1, and the other may not, or one or more phases may contain non-deformable and/or deformable visible beads, optionally in addition to the particles. The compositions of the present invention are able to maintain their visually distinguishable characteristics for prolonged periods of time including storage and transportation, without significant changes in their visual appearance, such as, for example, mixing to the extent that the visual patterns are completely obliterated. In various embodiments, shaking or agitation of the compositions may result in changes to the pattern of visual distinction, but visually distinguishable areas usually will still be discernible.

The embodiments of the present invention may additionally comprise additional materials such as solubilizers, pH adjusters (e.g., citric acid, HCl, NaOH, KOH), viscosity modifiers (e.g., isopropyl palmitate or isopropyl myristate), salts or other electrolytes (e.g., sodium chloride and other mono-, di- and trivalent salts), preservatives.

The compositions of the present invention may be in the form of any acceptable personal care compositions, including but not limited to: hair care products (e.g., shampoos, conditioners, mousses, sprays and hair gels), films, liquid soaps such as hand soaps and santizers, antiperspirants, deodorants, body washes, body gels, creams, lotions, bubble baths, bath powders, bath oils, and other portable forms.

In certain embodiments, the invention is directed to compositions of the present invention incorporated into one or more acceptable carriers. Acceptable carriers for the embodiments of the present invention may vary depending upon the composition and intended uses of a particular compound. Acceptable carriers for the personal care embodiments of the present invention should be ones that are dermatologically acceptable and not harsh when applied to the human skin, e.g., the skin of the scalp or other external regions of the human body for which personal care compositions are generally intended. Acceptable carriers for dentifrice compositions include orally acceptable vehicles.

Selection of specific carrier components is dependent on the desired product form. It should be understood that any suitable carrier known in the art or to be developed can be provided to the composition, and that the carrier or carriers useful for various embodiments of the present invention will depend upon the specific intended use of the compositions, and that one or more carriers may be suitable for overlapping intended uses.

The compositions of the present invention may also include one or more fragrances. Acceptable fragrances for the present invention include any fragrances that are pleasant and desirable for consumers and do not irritate or otherwise adversely affect the human body.

The compositions of the present invention may additionally include ingredients that may further enhance their desirability for consumers. For example, colorants, pH adjusters, preservatives, pearlescent or opacifying agents, thickening agents, conditioners, humectants, chelating agents/sequestrants, absorbents, abrasives, anticaking agents, anti-aging agents, astringents, antifoaming agents, binders, biological additives, buffering agents, bulking agents, chemical additives, colorants, cosmetic astringents, antimicrobial agents, denaturants, emollients, vitamins, foam boosters, sugars and starches, sugar and starch derivatives, hydrotropes, neutralizing agents, opacifying agents and pigments, plasticizers, propellants, reducing agents, skin tanning agents, skin bleaching agents, skin protectants, sunscreens, sunblocks and similar additives may be included in the compositions described herein and are contemplated by the present invention.

In another embodiment, the present invention provides a body wash comprising at least one surfactant and at least 1 weight % emollient that is solid below 50° C. that deposits less than 2 mg/cm$^2$ of the emollient on glass according to the Method for Residue Deposition on Glass for Liquid Body Cleansing Products, which is described in WO2009/117013, which is incorporated herein by reference in its entirety. In other embodiments, the amount of emollient is at least 2, 3, 4, 5, 6, 7, 8, 9, 10, 11, 12, 13, 14, 15, 20, 25, 30, 35, 40, 45, or 50 weight % of the composition.

When the compositions are dentifrice compositions, the various known dentifrice components, well known to those skilled in the art, may be selected from those known in the art, in addition to those described below. The dentifrice compositions described herein may be formulated with optional other ingredients, including without limitation anticaries agent, anticalculus or tartar control agents, anionic carboxylate polymers, viscosity modifiers, surfactants, flavorants, pigments, signals (flavor, color, light, heat, smell and other signals that signal the efficacious or advantageous use of the composition), agents to treat dry mouth, and the like.

In various embodiments, the compositions comprise an orally acceptable source of fluoride ions, which serves as an anticaries agent. One or more such sources can be present. Suitable sources of fluoride ions include fluoride, monofluorophosphate and fluorosilicate salts as well as amine fluorides, including olaflur (N'-octadecyltrimethylendiamine-N, N,N'-tris(2-ethanol)-dihydrofluoride).

As anticaries agent, one or more fluoride-releasing salts are optionally present in an amount providing a total of 100 to 20,000 ppm, 200 to 5,000 ppm, or 500 to 2,500 ppm, fluoride ions. Where sodium fluoride is the sole fluoride-releasing salt present, illustratively an amount of 0.01% to 5%, 0.05% to 1% or 0.1% to 0.5%, sodium fluoride by weight can be present in the composition. Other anticaries agents can be used, such as arginine and arginine derivatives (e.g., ethyl lauroyl arginine (ELAH)).

Phenolic compounds useful herein illustratively include, subject to determination of oral acceptability, those identified as having anti-inflammatory activity by Dewhirst (1980), Prostaglandins 20(2), 209-222, but are not limited thereto. Examples of antibacterial phenolic compounds include 4-allylcatechol, p-hydroxybenzoic acid esters including benzylparaben, butylparaben, ethylparaben, methylparaben and propylparaben, 2-benzylphenol, butylated hydroxyanisole, butylated hydroxytoluene, capsaicin, carvacrol, creosol, eugenol, guaiacol, halogenated bisphenolics including hexachlorophene and bromochlorophene, 4-hexylresorcinol, 8-hydroxyquinoline and salts thereof, salicylic acid esters including menthyl salicylate, methyl salicylate and phenyl salicylate, phenol, pyrocatechol, salicylanilide, and thymol.

The at least one phenolic compound is optionally present in a total amount of 0.01% to 10% by weight. Illustratively the total concentration of the at least one phenolic compound in a toothpaste or gel dentifrice or mouth rinse of the present invention can be 0.01 weight % to 5 weight %, for example 0.1 weight % to 2 weight %, 0.2 weight % to 1 weight % or 0.25 weight % to 0.5 weight %.

Other antibacterial agents that optionally may be used in addition to the natural extracts include, without limitation, copper (II) compounds such as copper (II) chloride, fluoride, sulfate and hydroxide, zinc ion sources such as zinc acetate, zinc citrate, zinc gluconate, zinc glycinate, zinc oxide, zinc sulfate and sodium zinc citrate, phthalic acid and salts thereof such as magnesium monopotassium phthalate, hexetidine, octenidine, sanguinarine, benzalkonium chloride, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, iodine, sulfonamides, bisbiguanides such as alexidine, chlorhexidine and chlorhexidine digluconate, piperidino derivatives such as delmopinol and octapinol, magnolia extract, grapeseed extract, menthol, geraniol, citral, eucalyptol, antibiotics such as augmentin, amoxicillin, tetracycline, doxycycline, minocycline, metronidazole, neomycin, kanamycin and clindamycin, and the like. A further illustrative list of useful antibacterial agents is provided in U.S. Pat. No. 5,776,435 to Gaffar et al. If present, these additional antimicrobial agents are present in an antimicrobial effective total amount, typically 0.05 weight % to 10 weight %, for example 0.1 weight % to 3 weight % by weight, of the composition.

In another embodiment the composition comprises an orally acceptable anticalculus agent. One or more such agents can be present. Suitable anticalculus agents include without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include anionic polycarboxylate polymers. The anionic polycarboxylate polymers contain carboxyl groups on a carbon backbone and include polymers or copolymers of acrylic acid, methacrylic, and maleic anhydride. Non-limiting examples include polyvinyl methyl ether/maleic anhydride (PVME/MA) copolymers, such as those available under the Gantrez™ brand from ISP, Wayne, N.J. Still other useful anticalculus agents include sequestering agents including hydroxycarboxylic acids such as citric, fumaric, malic, glutaric and oxalic acids and salts thereof, and aminopolycarboxylic acids such as ethylenediaminetetraacetic acid (EDTA). One or more anticalculus agents are optionally present in the composition in an anticalculus effective total amount, typically 0.01% to 50%, for example 0.05% to 25% or 0.1% to 15% by weight.

In various embodiments, the anticalculus system comprises a mixture of sodium tripolyphosphate (STPP) and a tetrasodium pyrophosphate (TSPP). In various embodiments, the ratio of TSPP to STPP ranges 1:2 to 1:4. In one embodiment, the first anticalculus active ingredient, TSPP is present at 1 to 2.5 weight % and the second anticalculus active ingredient, STPP is present at 1 to 10 weight %.

In one embodiment, the anionic polycarboxylate polymer is present 0.1 weight % to 5 weight %. In another embodiment, the anionic polycarboxylate polymer is present 0.5 weight % to 1.5 weight %, or at 1 weight % of the oral care composition. In one embodiment according to the present invention, the anticalculus system comprises a copolymer of maleic anhydride and methyl vinyl ether, such as for example, the Gantrez™ S-97 product discussed above.

In various embodiments, the ratio of TSPP to STPP to the synthetic anionic polycarboxylate ranges 5:10:1 to 5:20:10 (or 1:4:2). In one embodiment, the anticalculus system of the oral care composition comprises TSPP, STPP, and a polycarboxylate such as a copolymer of maleic anhydride and methyl vinyl ether at a ratio of 1:7:1. In a non-limiting embodiment, the anticalculus system consists essentially of TSPP present at 0.5 weight % to 2.5 weight %, STPP present at 1 weight % to 10 weight %, and a copolymer of maleic anhydride and methyl vinyl ether present at 0.5 weight % to 1.5 weight %

In another embodiment the composition comprises an orally acceptable stannous ion source useful, for example, in helping reduce gingivitis, plaque, calculus, caries or sensitivity. One or more such sources can be present. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of 0.01 weight % to 10 weight %, for example 0.1 weight % to 7 weight % or 1 weight % to 5 weight % by weight of the composition.

In another embodiment the composition comprises an orally acceptable zinc ion source useful, for example, as an antimicrobial, anticalculus or breath-freshening agent. One or more such sources can be present. Suitable zinc ion sources include without limitation zinc acetate, zinc citrate, zinc gluconate, zinc glycinate, zinc oxide, zinc sulfate, sodium zinc citrate and the like. One or more zinc ion sources are optionally and illustratively present in a total amount of 0.05 weight % to 3 weight %, for example 0.1 weight % to 1 weight %, by weight of the composition.

In another embodiment the composition comprises an orally acceptable breath-freshening agent. One or more such agents can be present in a breath-freshening effective total amount. Suitable breath-freshening agents include without limitation zinc salts such as zinc gluconate, zinc citrate and zinc chlorite, α-ionone and the like.

In another embodiment the composition comprises an orally acceptable antiplaque, including plaque disrupting, agent. One or more such agents can be present in an antiplaque effective total amount. Suitable antiplaque agents include without limitation stannous, copper, magnesium and strontium salts, ionic liquids, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof.

In another embodiment the composition comprises an orally acceptable anti-inflammatory agent other than the rosemary components described above. One or more such agents can be present in an anti-inflammatory effective total amount. Suitable anti-inflammatory agents include without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

Compositions of the inventions optionally contain other ingredients such as enzymes, vitamins and anti-adhesion agents. Enzymes such as proteases can be added for anti-stain and other effects. Non-limiting examples of vitamins include vitamin C, vitamin E, vitamin E acetate (a Vitamin E precursor), vitamin B5, and folic acid. In various embodiments, the vitamins have antioxidant properties. Anti-adhesion agents include ethyl lauroyl arginine (ELAH), ficin, silicone polymers and derivatives, and quorum sensing inhibitors.

Among useful carriers for optional inclusion in a composition of the invention are diluents, abrasives, bicarbonate salts, pH modifying agents, surfactants, foam modulators, thickening agents, viscosity modifiers, humectants, sweeteners, flavorants and colorants. One carrier material, or more than one carrier material of the same or different classes, can optionally be present. Carriers should be selected for compatibility with each other and with other ingredients of the composition.

Water is a preferred diluent and in some compositions such as mouthwashes and whitening liquids is commonly accompanied by an alcohol, e.g., ethanol. The weight ratio of water to alcohol in a mouthwash composition is generally 1:1 to 20:1, for example 3:1 to 20:1 or 4:1 to 10:1. In a whitening liquid, the weight ratio of water to alcohol can be within or below the above ranges, for example 1:10 to 2:1.

In one embodiment a composition of the invention comprises at least one abrasive, useful for example as a polishing agent. Any orally acceptable abrasive can be used, but type, fineness (particle size) and amount of abrasive should be selected so that tooth enamel is not excessively abraded in normal use of the composition. Suitable abrasives include without limitation silica, for example in the form of silica gel, hydrated silica or precipitated silica, alumina, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in an abrasive effective total amount, typically 5 weight % to 70 weight %, for example 10 weight % to 50 weight % or 15 weight % to 30 weight % by weight of the composition. Average particle size of an abrasive, if present, is generally 0.1 to 30 µm, for example 1 to 20 µm or 5 to 15 µm.

In a further embodiment a composition of the invention comprises at least one bicarbonate salt, useful for example to impart a "clean feel" to teeth and gums due to effervescence and release of carbon dioxide. Any orally acceptable bicarbonate can be used, including without limitation alkali metal bicarbonates such as sodium and potassium bicarbonates, ammonium bicarbonate and the like. One or more bicarbonate salts are optionally present in a total amount of 0.1 weight % to 50 weight %, for example 1 weight % to 20 weight % by weight of the composition.

In a still further embodiment a composition of the invention comprises at least one pH modifying agent. Such agents include acidifying agents to lower pH, basifying agents to raise pH and buffering agents to control pH within a desired range. For example, one or more compounds selected from acidifying, basifying and buffering agents can be included to provide a pH of 2 to 10, or in various illustrative embodiments 2 to 8, 3 to 9, 4 to 8, 5 to 7, 6 to 10, 7 to 9, etc. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in an orally acceptable pH range.

In a still further embodiment a composition of the invention comprises at least one surfactant, useful for example to compatibilize other components of the composition and thereby provide enhanced stability, to help in cleaning the dental surface through detergency, and to provide foam upon agitation, e.g., during brushing with a dentifrice composition of the invention. Any orally acceptable surfactant, most of which are anionic, nonionic or amphoteric, can be used. Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like. Suitable amphoteric surfactants include without limitation derivatives of $C_{8-20}$ aliphatic secondary and tertiary amines having an anionic group such as carboxylate, sulfate, sulfonate, phosphate or phosphonate. A suitable example is cocoamidopropyl betaine. One or more surfactants are optionally present in a total amount of 0.01 weight % to 10 weight %, for example 0.05 weight % to 5 weight % or 0.1 weight % to 2 weight % by weight of the composition.

In a still further embodiment a composition of the invention comprises at least one foam modulator, useful for example to increase amount, thickness or stability of foam generated by the composition upon agitation. Any orally acceptable foam modulator can be used, including without limitation polyethylene glycols (PEGs), also known as polyoxyethylenes. High molecular weight PEGs are suitable, including those having an average molecular weight of 200,000 to 7,000,000, for example 500,000 to 5,000,000 or 1,000,000 to 2,500,000. One or more PEGs are optionally present in a total amount of 0.1 weight % to 10 weight %, for example 0.2 weight % to 5 weight % or 0.25 weight % to 2 weight % by weight of the composition.

In a still further embodiment a composition of the invention comprises at least one thickening agent, useful for example to impart a desired consistency and/or mouth feel to the composition. These thickening agents increase the yield point of the compositions so that the composition can support the particles dispersed therein. Any orally acceptable thickening agent can be used, including without limitation carbomers, also known as carboxyvinyl polymers, carrageenans, also known as Irish moss and more particularly t-carrageenan (iota-carrageenan), cellulosic polymers such as hydroxyethylcellulose, carboxymethylcellulose (CMC) and salts thereof, e.g., CMC sodium, natural gums such as karaya, xanthan, gum arabic and tragacanth, colloidal magnesium aluminum silicate, colloidal silica and the like. One or more thickening agents are optionally present in a total amount of 0.01 weight % to 15 weight %, for example 0.1 weight % to 10 weight % or 0.2 weight % to 5 weight % by weight of the composition.

In a still further embodiment a composition of the invention comprises at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like. One or more viscosity modifiers are optionally present in a total amount of 0.01 weight % to 10 weight %, for example 0.1 weight % to 5 weight % by weight of the composition.

In a still further embodiment a composition of the invention comprises at least one humectant, useful for example to prevent hardening of a tooth paste upon exposure to air. Any orally acceptable humectant can be used, including without limitation polyhydric alcohols such as glycerin, sorbitol, xylitol or low molecular weight PEGs. Most humectants also function as sweeteners. One or more humectants are optionally present in a total amount of 1 weight % to 70 weight %, for example 1 weight % to 50 weight %, 2 weight % to 25 weight %, or 5 weight % to 15 weight % by weight of the composition.

In a still further embodiment a composition of the invention comprises at least one sweetener, useful for example to enhance taste of the composition. Any orally acceptable natural or artificial sweetener can be used, including without limitation dextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, cyclamates and the like. One or more sweeteners are optionally present in a total amount depending strongly on the particular sweetener(s) selected, but typically 0.005 weight % to 5 weight % by weight of the composition.

In a still further embodiment a composition of the invention comprises at least one flavorant, useful for example to enhance taste of the composition. Any orally acceptable natural or synthetic flavorant can be used, including without limitation vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, $\alpha$-irisone, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), menthone glycerol acetal (MGA) and the like. One or more flavorants are optionally present in a total amount of 0.01 weight % to 5 weight %, for example 0.1 weight % to 2.5 weight % by weight of the composition.

In another embodiment, mouthwash or mouth rinse compositions are provided that contain water, one or more particles having an aspect ratio greater than 1, one or more flavorants such as discussed above, one or more organic hydric compounds, and an antibacterial effective amount of an antibacterial composition as discussed above. The one or more organic hydric compounds are orally acceptable organic solvents such as, without limitation, ethanol and glycerol. Optionally, the mouthwash and mouth rinse compositions contain a surfactant to aid in dispersal of the flavorants and antibacterial compositions.

While not intending on being bound by any theory of operation, the inventors believe that the method orients the particles due to the stresses exerted on the particles during transport. That is, as the structured composition having a desired yield point containing the particles is transported along a feed pipe or tube, for example, the flow of the composition creates stresses along the direction of the flow (as defined in, for example, Navier-Stokes equations), and because of the high aspect ratio of the particles, the particles tend to orient themselves in the direction of the flow. By orienting themselves, the particles will orient in a manner that the particles' major dimension (labeled "D" in particle 65 in FIG. 1) will be substantially parallel to the direction of flow. Such an orientation can create an aesthetically attractive product when the phases are swirled together or form some other form of visually distinguishable phase separation.

The stress, or force, required to orient the particles, and/or deform deformable beads, is dependent upon the flow rate of the fluid through the pipe, as well as many other factors such as the yield point, viscosity, shape of pipes, etc. In certain embodiments, the compositions when flowing through the pipes, do not create turbulent flow, or if turbulence is created, it is minimal. In certain embodiments, the flow is laminar. In certain embodiments, such flow can be maintained by providing at least one composition having a viscosity of at least 10,000 mPas at room temperature and a yield point of at least 3 Pa at room temperature (if below get turbulent flow). At laboratory scale, the flow rate is 10-150 ml/s, or 40-80 ml/s in other embodiments.

In certain embodiments, the orientation of the particles or the distinguishable pattern can be maintained during transportation and storage of the composition. For transportation tests, the tests from the International Safe Transit Association (ISTA) can be used.

The embodiments also include methods of making a visually patterned oriented composition that includes:
  a) preparing at least a first composition comprised of a first vehicle and particles having an aspect ratio greater than 1;
  b) preparing at least a second composition comprised of at least a second vehicle; and
  c) dispensing the at least first composition and the at least second composition into a container in a manner that provides at least a first visually distinguishable zone comprised of the at least first composition in which the particles are oriented in a plane substantially parallel to the plane of flow of the first composition, and at least a second visually distinguishable zone comprised of the at least second composition, the at least second visually distinguishable zone in contact with the at least first visually distinguishable zone, wherein the at least first visually distinguishable zone and the at least second visually distinguishable zone form a visibly distinguishable pattern.

In the single composition embodiment, the method includes flowing the composition under non-turbulent conditions as described above to orient the visible particles.

The composition can be packaged in a container. The container can be of a size that is used for selling materials to consumers, such as those having a volume of 10 ml to 200 liters.

By way of example, and not limitation, specific embodiments of the present invention are illustrated in the following Examples. In the examples, the amounts of the materials listed are by weight as supplied. In the remainder of the specification and the claims, the amount of material is based on the active weight of the material.

SPECIFIC EMBODIMENTS

The invention is further described in the following examples of formula bases to which particulates can be incorporated. The examples are merely illustrative and do not in any way limit the scope of the invention as described and claimed.

Example 1

The following materials shown in Table 1 are mixed together to form compositions in accordance with the present invention and include optional materials. All percentages are by weight. The amount of water is listed, but the amount of water could alternatively be q.s. (quantum suficit).

The following procedure was used for Formulas A-C:
1. Heat water to 40° C.
2. Add clay and stir until fully dispersed, when solution becomes transparent.
3. Heat Solution to 60-65° C.
4. Add crosslinked polycarboxylate associative thickener with constant stirring.
5. Turn off heater.
6. Add SLES (sodium lauryl ether sulfate) with stirring.
7. Add cocoamidopropylbetaine with stirring.
8. Add EDTA with stirring.
9. Reduce solution temperature to below 40° C.
10. Add DMDM Hydantoin with stirring.
11. Adjust solution pH to 8.0 with NaOH and citric Acid.
12. Add Polyquat-7 with stirring.
13 Add Sunflower Oil to formula with stirring.
14. Make pre-mix of Petrolatum, Ceraphyl™-RMT, and Silicone Elastomer by melting at 49° C., and add to solution with stirring.
15. Add fragrance with stirring.
16. Make final adjustment to formula pH with NaOH and/or Citric Acid.

TABLE 1

| Ingredients | A | B | C |
| --- | --- | --- | --- |
| Deionized Water | Q.S. (about 52.374) | Q.S. (about 52.324) | Q.S. (about 51.924) |
| Clay | 0.300 | 0.300 | 0.300 |
| Crosslinked Polycarboxylate Associative Thickener | 4.250 | 4.250 | 4.250 |
| SLES(SO3Na Pareth 145-2EO Sulfate Base-25.5% AI) | 26.002 | 26.002 | 26.002 |
| Cocoamidopropyl Betaine (Coco Fatty Acid, Topped, Hydrogenated) | 8.878 | 8.878 | 8.878 |
| PolyQuat-7 | 1.200 | 1.200 | 1.200 |
| Tetrasodium EDTA-39% AI | 0.200 | 0.200 | 0.200 |
| DMDM Hydantoin | 0.500 | 0.500 | 0.500 |
| Ceraphyl ™-RMT | 0.050 | 0.100 | 0.500 |
| Sunflower Oil | 1.420 | 1.420 | 1.420 |
| Petrolatum | 3.000 | 3.000 | 3.000 |
| Silicone Elastomer | 0.08 | 0.08 | 0.08 |
| NaOH (50% in $H_2O$) | 0.600 | 0.600 | 0.600 |
| Citric Acid | 0.146 | 0.146 | 0.146 |
| Fragrance | 1.000 | 1.000 | 1.000 |

The following procedure was used for Formulas D thru G:
1. Add the EDTA and Glycerin to the Water
2. Add clay and heat to 40° C.
3. Stir until fully dispersed, when solution becomes transparent.
4. Heat Solution to 40° C.
5. Add SLES (sodium lauryl ether sulfate) with stirring.
6. Turn off heater.
7. Add the Kathon CG
8. Add crosslinked polycarboxylate associative thickener with constant stirring.
9. Adjust solution pH to 6.8 using NaOH
10. Add cocoamidopropylbetaine with stirring.
11. Reduce solution temperature to below 40° C.
12. Add Polyquat-7 with stirring.
13. Make pre-mix of Sunflower Oil, Ceraphyl™-RMT, and Vitamin E Acetate if required in the formula, and add to solution with stirring.
14. Make pre-mix of Petrolatum, Ceraphyl™-RMT, and Vitamin E Acetate if require in the formula and no sunflower Oil is used by melting at 70 to 80° C., and add to solution with stirring.
15. Add the Maltose to the solution and stir.
16. Add fragrance with stirring.
17. Deareate the solution as required using appropriate methods known to thoses skilled in the art.

| Ingredients | D | E | F | G |
| --- | --- | --- | --- | --- |
| Deionized Water | Q.S. (about 63.785) | Q.S. (about 66.785) | Q.S. (about 64.535) | Q.S. (about 67.535) |
| Clay | 0.250 | 0.250 | 0.250 | 0.250 |
| Crosslinked Polycarboxylate Associative Thickener | 3.65 | 3.65 | 3.65 | 3.65 |
| SLES(C12-14 ALCOHOL EO 2:1 NA SULPHATE-70% AI) | 9.500 | 9.500 | 9.500 | 9.500 |
| Cocoamidopropyl Betaine (Coco Fatty Acid, Topped, Hydrogenated) | 8.000 | 8.000 | 8.000 | 8.000 |
| PolyQuat-7 | 1.200 | 1.200 | 1.200 | 1.200 |
| Tetrasodium EDTA-39% AI | 0.200 | 0.200 | 0.200 | 0.200 |
| Kathon CG | 0.080 | 0.080 | 0.080 | 0.080 |
| Ceraphyl ™-RMT | 0.010 | 0.100 | 0.100 | 0.100 |
| Sunflower Oil | 0.750 | 0.750 | 0.000 | 0.000 |
| Petrolatum | 3.000 | 0.000 | 3.000 | 0 |
| Vitamin E Acetate | 0.02 | 0.02 | 0.02 | 0.02 |
| NaOH (50% in $H_2O$) | 0.155 | 0.155 | 0.155 | 0.155 |
| Glycerin | 2.700 | 2.700 | 2.700 | 2.700 |

-continued

| Ingredients | D | E | F | G |
|---|---|---|---|---|
| Maltose (Satin Sweet 65% High Maltose Corn Syrup) | 5.7 | 5.7 | 5.7 | 5.7 |
| Fragrance | 1.000 | 1.000 | 1.000 | 1.000 |

Figure 1A:
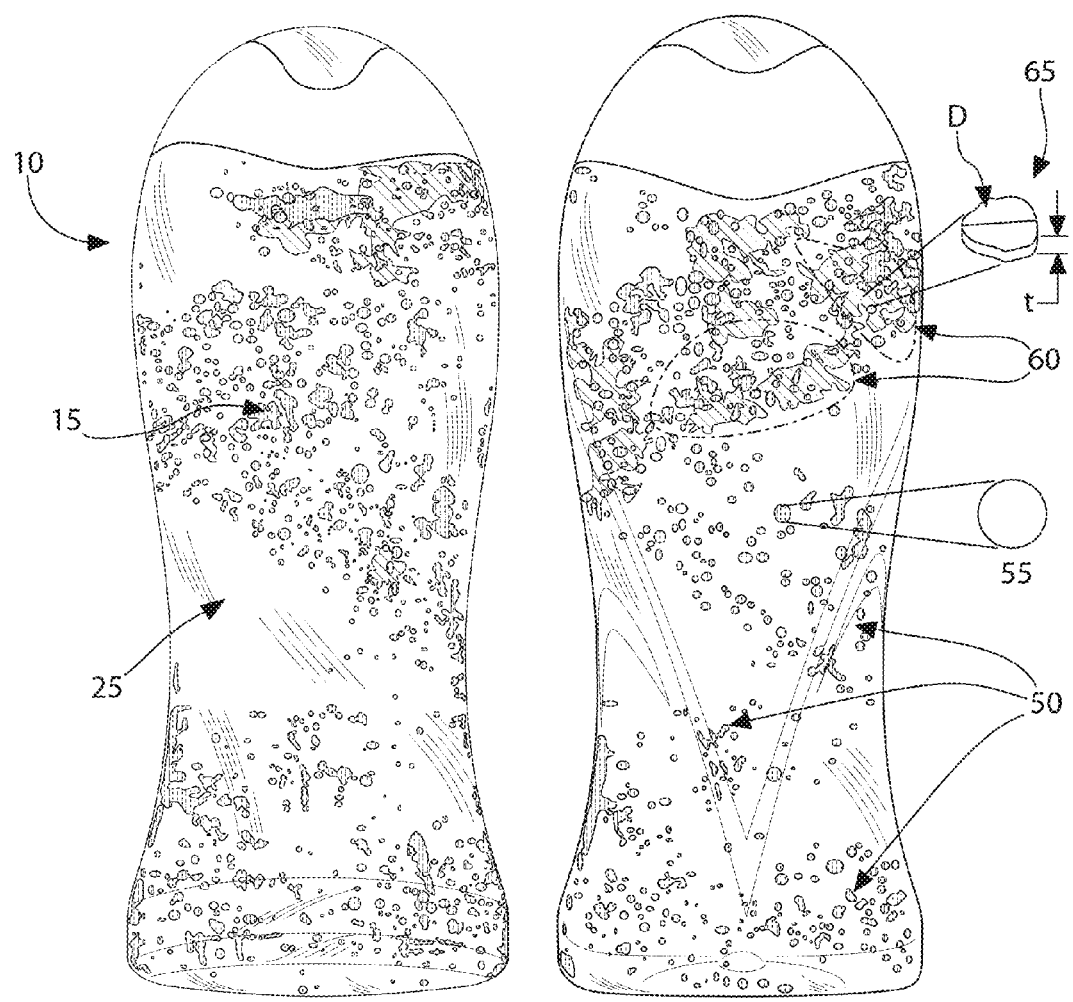

FIGS. 1 and 1A show a front and back view of a container filled with the two-phase composition of the above example. The container used in FIGS. 1 and 1A is the container from U.S. Design Pat. No. D608647. Container 10 includes the composition that comprises two visibly distinguishable zones 15, 25. Zone 15 includes the high aspect ratio particles and the visible beads, whereas zone 25 includes the same base as zone 15, but does not contain the high aspect ratio particles 65 and the visible beads 50. While not clearly shown in the greyscale of FIG. 1, the visible beads 50 (55) have a distinguishable color that serves to further distinguish the respective phases, and the high aspect ratio particles 65 provide certain areas of color by virtue of reflecting light. The front view of container 10 is provided on the left, whereas the back view is shown on the right.

The back view on the right of FIG. 1 shows reflective regions 60 that are not seen in the front view. This is due to the orientation of the high aspect ratio particles 65, which are shown in an exploded view to the right of FIG. 1. The visible beads 55 also generally are spherically shaped, as shown in the exploded view to the right of FIG. 1. Both views shown in FIG. 1 reveal distinguishable and separate zones 15, 25, that provides an aesthetically unique design characteristic to the product, and because the color or reflective character of the particles changes when the viewing angle changes, the compositions can promote product identification for the manufacturer.

Example 2

Figure 2:
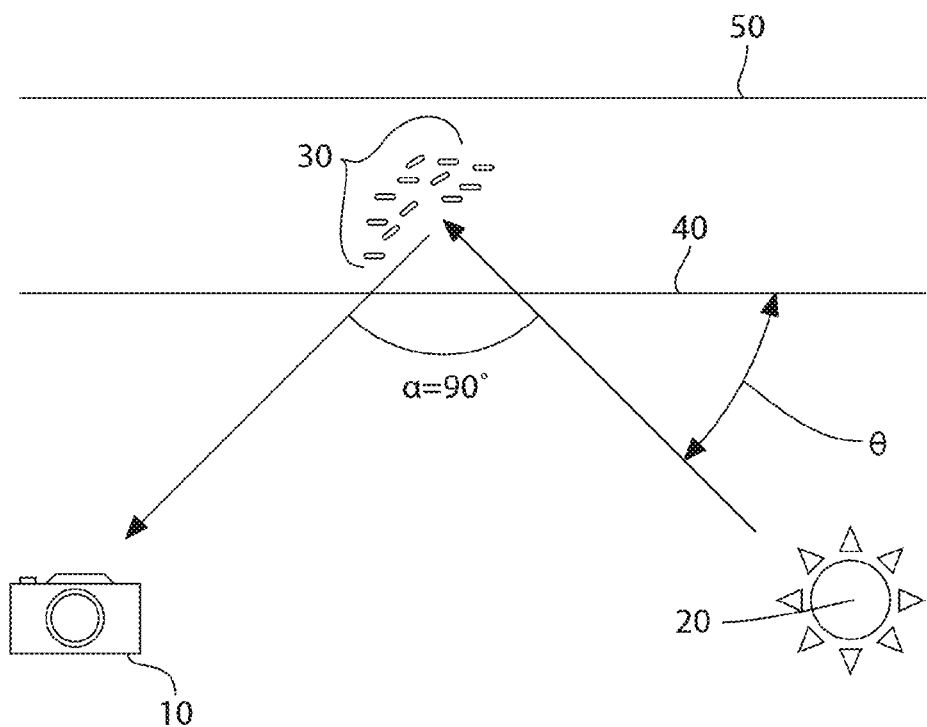
FIG. 2 is a schematic of the apparatus used in the examples to measure specular reflectance from a sample at different angles.

To demonstrate the orientation of the particles, an apparatus is set up to measure the amount of reflectance of particles in Formula B above in an oriented configuration as compared to an unoriented configuration. An inventive composition is prepared similar to that shown in FIG. 1 with oriented particles prepared using laminar flow. The composition is contained in the same container (see U.S. Design Pat. No. D608647) as Example 1. The same composition is used to prepare a comparative composition with unoreiented particles using non-laminar flow, which is contained in a cylindrical container. An apparatus shown in FIG. 2 is set up, which is described below.

Experimental Set-up and Image Capture
1. Set up experiment as displayed in FIG. 2.
2. This experiment uses a clear primary structured phase with a "swirled" secondary phase containing the reflective particles from Example 1 above. Opacity can also be incorporated into the secondary phase. A completely opaque product can also be measured by detecting reflective particles at the interface of the product and the inner wall of the bottle. In addition, a single phase product can also be used where the particles are oriented upon filling into the bottle. This product requires a structured system that is capable of supporting the reflective particles in sample.
3. Specular reflectance is defined as a mirror like reflection.
4. In addition to specular reflectance, particles can also be made of materials which exhibit other reflective properties which allow visual discrimination versus the bulk product. For example, the particles could be of a different colors and or textures compared to the bulk product.
5. The bottle containing reflective particles is place on a rotating base with angular demarcations of 1 degree.
6. The settings below are used for this experiment example. These settings were selected based on the criteria described below. The camera settings are optimized so that the particles exhibiting specular reflectance in an image produce close to a maximum in the gray scale of the image.
   Both the camera detector and the tungsten light source are placed approximately 38 cm (15 inches) from the front plane of the bottle containing the sample.
   Camera: 10 megapixel Cannon Rebel Digital SLR
   Lens: 50 mm, macro
   F stop: f20
   Shutter speed: 1/20 sec
   ISO: 800
   Light Source Tungsten light with conical reflector behind the light source.
   Photograph as a color image.
7. Set the angle between the axes of the light source and the camera with respect to the surface of the bottle at 90 degrees. See FIG. 2. The illumination angle θ shown in FIG. 2 is 45 degrees. The illumination angle θ is the angle formed between the wall of the container and the light source.
8. Focus the camera on the front surface of the bottle.
9. Calibrate the angle reading of the bottle position by rotating the bottle until maximum specular reflectance is observed at the center of the field of view of the camera. Readings of raw angles from the rotating container are then adjusted for the calculated offset.
10. Focus the camera on a region of interest (ROI) in the sample.
11. Adjust the shutter speed to optimize the discrimination between the background image and the portions of the region of the image that are due to specular reflectance from the small asymmetric reflective particles in solution. It is desirable to use as large an f stop number as possible to ensure maximize the depth of field in focus. Shutter speed and f stop will depend on the illumination conditions for the experiment, for example: lamp wattage, exact distance from the light source and the region of interest, and the exact distance from the bottle region of interest and the camera.
12. Identify a rectangular projection of the region of interest on the front bottle surface by placing a small visible dot at each corner. The projected region of interest should be of appropriate size to meet the following conditions:
    a. The ROI should maximize use of the detector area by maximizing the area in the field of view the ROI covers.
    b. The ROI should be of appropriate size that the complete ROI can be measured at all rotation angles used in the experiment.
    c. The focal plan of the camera should be set to the point of the center of bottle rotation. This is accomplished by manually rotating the bottle and ensuring that identified structures in the focal plain determined to be particles exhibiting specular relectance remain in focus and centered in the field of view measured both vertically and horizontally.
13. Minimize extraneous sources of light to optimize the angular resolution and detection of specular reflectance.
14. Rotate the bottle in 5 degree increments and capture a digital image at each measurement angle.

Figure 3:
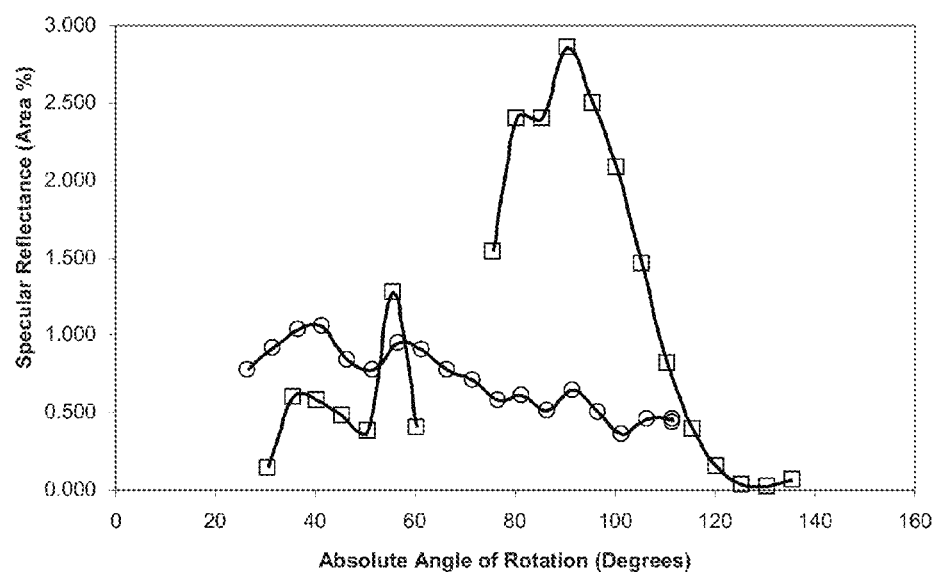
FIG. 3 is a graph of specular reflectance at different angles from data generated by an example. Inventive marked with squares, and comparative marked with circles.

Image and Data Analysis
1. Adobe PhotoShop is recommended as the software of choice for image analysis.
2. Identify and delineate the ROI in each image using the dots placed on the bottle surface as a guide for drawing a rectangular area for measurement. Measure the total number of pixels in the ROI.
3. Convert the image to gray scale. If a visual property of the particles other than specular reflectance is to be measured. The images should not be converted to gray scale, but retained as color images.
4. Identify the particles in the ROI using histogram segmentation.
5. Use the select color range function to highlight the particles and identify a selection of gray scale (or for color images a combination of color and gray scale) intensities that maximizes the isolation of the particles from the rest of the image. The fuzziness setting within the color selection function is used to maximize selection of particles that exhibit specular reflectance to correlate with that which is observed visually. Without the fuzziness setting, only a specific L-a-b setting would be selected. With the fuzziness setting, a range of L-a-b values can be selected. This is adjusted until the digital selection of particles matches what is seen visually.
6. Set up a table for the number of pixels detected in each image ROI and the angle of illumination (as calculated above).
7. Convert the number of specular reflectance pixels to the Area % Specular reflectance by dividing the number of pixels exhibiting specular reflectance by the total number of pixels in the delineated ROI. See Table 2 below. The data below are shown graphically in FIG. 3.

TABLE 2

| Random Particles | | Oriented Particles | |
| --- | --- | --- | --- |
| angle of Illumination | Specular Reflectance (area %) | angle of Illumination | Specular Reflectance (area %) |
|  |  | 135.5 | 0.06377 |
|  |  | 130.5 | 0.02140 |
|  |  | 125.5 | 0.03738 |
| 111.5 | 0.433 | 120.5 | 0.14813 |
| 111.5 | 0.463 | 115.5 | 0.39100 |
| 106.5 | 0.456 | 110.5 | 0.81982 |
| 101.5 | 0.357 | 105.5 | 1.45945 |
| 96.5 | 0.497 | 100.5 | 2.08209 |
| 91.5 | 0.639 | 95.5 | 2.50279 |
| 86.5 | 0.515 | 90.5 | 2.85492 |
| 81.5 | 0.607 | 85.5 | 2.39866 |
| 76.5 | 0.578 | 80.5 | 2.40112 |
| 71.5 | 0.704 | 75.5 | 1.53440 |
| 66.5 | 0.780 | 70.5 |  |
| 61.5 | 0.911 | 65.5 |  |
| 56.5 | 0.953 | 60.5 | 0.39903 |
| 51.5 | 0.778 | 55.5 | 1.27864 |
| 46.5 | 0.838 | 50.5 | 0.37785 |
| 41.5 | 1.062 | 45.5 | 0.48284 |
| 36.5 | 1.039 | 40.5 | 0.58166 |
| 31.5 | 0.915 | 35.5 | 0.59995 |
| 26.5 | 0.780 | 30.5 | 0.14271 |

Also contemplated are methods for making any of the structured systems and personal care or dentifrice compositions of the present invention, as well as methods of optimizing the viscosity of a composition to improve filling of systems having varying visibly distinguishable areas.

What is claimed is:

1. A visually patterned oriented composition comprising:
   a) at least a first visually distinguishable zone comprising visible particles having an aspect ratio greater than 1.5:1 and a particle size of 50 µm to 5000 µm in a longest dimension, the visible particles having their larger dimension oriented in a plane substantially parallel to the plane of flow of the first visually distinguishable zone; and
   b) at least a second visually distinguishable zone in physical contact with the at least first visually distinguishable zone,
   wherein the at least first visually distinguishable zone and the at least second visually distinguishable zone form a visibly distinguishable pattern, wherein the composition includes a crosslinked polycarboxylate thickener as a structural material, present in the at least first visually distinguishable zone, that retains the orientation of the visible particles in the composition, wherein the composition is packaged in a container using laminar flow; substantially means that the visible particles plane and the plane of flow do not intersect within the container, and wherein the visually patterned oriented composition is a liquid, a gel or a foam.

2. The composition of claim 1, wherein at least 50% of the visible particles have their x-y planes substantially parallel, parallel, or coincident to x-y planes of the other visible particles, and substantially means that the x-y planes of the visible particles do not intersect within the container.

3. The composition of claim 1, wherein the visible particle comprises at least one particle chosen from films, metallic particles, naturally reflective particles, interference pigments, multi-layered pigments, solid and liquid crystals, visible beads, deformable visible beads, mica, metallic films, silicates, borosilicates, glass, and mixtures or combinations thereof.

4. The composition of claim 3, wherein the visible particle is selected from visible beads, deformable visible beads, mica, and/or metallic films.

5. The composition of claim 4, wherein the visible particle is mica.

6. The composition of claim 5, further comprising a visible bead.

7. The composition of claim 1, wherein the visible particle has an aspect ratio of 2:1 or greater.

8. The composition of claim 1, wherein the visible particle has an aspect ratio greater than 15:1.

9. The composition of claim 1, wherein at least the first visually distinguishable zone has a yield point of 3 to 100 Pa at room temperature.

10. The composition of claim 1, wherein at least the first visually distinguishable zone has a viscosity of at least 10,000 mPas at room temperature.

11. A method of making the visually patterned oriented composition of claim 1 comprising:
   a) preparing at least a first composition comprised of a first vehicle and visible particles having an aspect ratio greater than 1.5:1 and a particle size of 50 µm to 5000 µm in a longest dimension;
   b) preparing at least a second composition comprised of at least a second vehicle; and c) dispensing the at least first composition and the at least second composition into a container using laminar flow in a manner that provides the at least first visually distinguishable zone comprised of the at least first composition in which the visible particles are oriented in a plane substantially parallel to the plane of flow of the first composition, and the at least second visually distinguishable zone comprised of the at least second composition, the at least second visually distinguishable zone in contact with the at least first visually distinguishable zone, wherein the at least first visually distinguishable zone and the at least second visually distinguishable zone form a visibly distinguishable pattern, and wherein the composition includes a crosslinked polycarboxylate thickener as a structural material, present in the at least first visually distinguishable zone, that retains the orientation of the visible particles in the composition, and substantially means that the visible particles plane and the plane of flow do not intersect within the container, and wherein the visually patterned oriented composition is a liquid, a gel or a foam.

12. The method of claim 11, wherein the visible particle comprises at least one particle chosen from films, metallic particles, naturally reflective particles, interference pigments, multi-layered pigments, solid and liquid crystals, visible beads, deformable visible beads, mica, metallic films, silicates, borosilicates, glass, and mixtures or combinations thereof.

13. The method of claim 12, wherein the visible particle is selected from visible beads, deformable visible beads, mica, and/or metallic films.

14. The method of claim 13, wherein the visible particle is mica.

15. The method of claim 14, further comprising a visible bead.

16. The method of claim 11, wherein the visible particle has an aspect ratio of 2:1 or greater.

17. The method of claim 11, wherein the visible particle has an aspect ratio greater than 15:1.

18. The method of claim 11, wherein at least the first visually distinguishable zone has a yield point of 3 to 100 Pa at room temperature.

19. The method of claim 11, wherein at least the first visually distinguishable zone has a viscosity of at least 10,000 mPas at room temperature.

20. The method of claim 11, wherein at least 50% of the visible particles have their x-y planes substantially parallel, parallel, or coincident to x-y planes of the other visible particles, and substantially means that the x-y planes of the visible particles do not intersect within the container.

21. The composition of claim 1, wherein the crosslinked polycarboxylate thickener is present in an amount of 1 to 7.5 weight % based on the weight of the composition.

* * * * *